(12) United States Patent
Guarna et al.

(10) Patent No.: US 7,625,892 B2
(45) Date of Patent: Dec. 1, 2009

(54) PHARMACEUTICAL COMPOSITIONS FOR THE TREATMENT OF DISEASES RELATED TO NEUROTROPHINES

(75) Inventors: Antonio Guarna, Seano (IT); Federico Cozzolino, Caldine Fiesole (IT); Maria Torcia, Florence (IT); Enrico Garaci, Rome (IT)

(73) Assignee: Mimetech S.r.l., Florence (IT)

( * ) Notice: Subject to any disclaimer, the term of this patent is extended or adjusted under 35 U.S.C. 154(b) by 0 days.

(21) Appl. No.: 10/518,689

(22) PCT Filed: Jun. 18, 2003

(86) PCT No.: PCT/EP03/06471

§ 371 (c)(1),
(2), (4) Date: Dec. 17, 2004

(87) PCT Pub. No.: WO04/000324

PCT Pub. Date: Dec. 31, 2003

(65) Prior Publication Data

US 2006/0069092 A1    Mar. 30, 2006

(30) Foreign Application Priority Data

Jun. 19, 2002   (IT)  ............................ FI2002A0107

(51) Int. Cl.
| | |
|---|---|
| A61K 31/535 | (2006.01) |
| A01N 43/42 | (2006.01) |
| A61K 31/00 | (2006.01) |
| A01N 43/00 | (2006.01) |
| A01N 43/62 | (2006.01) |
| C07D 498/00 | (2006.01) |
| C07D 513/00 | (2006.01) |
| C07D 515/00 | (2006.01) |
| C07D 243/00 | (2006.01) |
| C07D 257/00 | (2006.01) |

(52) U.S. Cl. ............... 514/230.5; 514/304; 514/211.01; 514/221; 540/552; 540/567

(58) Field of Classification Search ................ 514/304, 514/211.01, 230.5, 221; 540/552, 567
See application file for complete search history.

(56) References Cited

U.S. PATENT DOCUMENTS 4,463,004 A * 7/1984 Guerret et al. ............... 514/183
2003/0176414 A1 * 9/2003 Guarna et al. ........... 514/211.09

FOREIGN PATENT DOCUMENTS

WO      WO 01/64686    *   9/2001

OTHER PUBLICATIONS

Guarna et al. J. Org. Chem. 1999, 64, 7347-7364.*
Van Cauwenberghe et al. Heterocycles 1975, 3, 101-107.*
May et al. J. Pharmaceutical Sciences 1968, 57, 511-513.*
Guidi et al. Arch. Pharm. Pharm. Med. Chem. 1997, 330, 201-202.*
Wang et al. J. Chem. Soc., Perkin Trans. 1, 1996, 1,209-212.*
Guarna et al. Tetrahedron: Asymmetry 2000, 11, 4227-4238.*
Scarpi et al. Bioorg. Med. Chem. 2001, 9, 1625-1632.*
Machetti et al. Org. Lett. 2000, 2, 3987-3990.*
Cini et al (Eur J of Org Chem, Mar. 2002, 873-880).*
Guarna et al., "Synthesis and Reactivity of Bicycles Derived from Tartaric Acid and alpha-Amino Acids: A Novel Class of Conformationally Constrained Dipeptide Isosteres Based upon Enantiopure 3-Aza-6,8-dioxabicyclo[3.2.1]octane-7-carboxylic Acid," J. Organic Chemistry 64:7347-7364, 1999.
Machetti et al., "Oligomers of Enantiopure Bicyclic gamma/delta-Amino Acids (BTAa). 1. Synthesis and Conformational Analysis of 3-Aza-6,8-dioxabicyclo[3.2.1]octane-7-carboxylic Acid Oligomers (PolyBTG)," Organic Letters 2(25):3987-3990, 2000.
May et al., "Cholinergic Receptor I. Cholinomimetic Activities of Some Analogs of cis-2-Methyl-4-dimethylaminomethyl-1,3-dioxolane Methiodide," J. Pharmaceutical Sciences 57(3):511-513, 1968.

* cited by examiner

Primary Examiner—Sreeni Padmanabhan
Assistant Examiner—Umamaheswari Ramachandran
(74) Attorney, Agent, or Firm—Clark & Elbing LLP

(57) ABSTRACT

The present invention refers to pharmaceutical preparations including as active compounds 3-aza-bicyclo[3.2.1]octane derivatives of general formula (I) and/or their dimers of general formula (II) and (III) acting as agonists of human neurotrophines. Therefore, such compounds of formula (I), (II) and (III) are useful for treatment of diseases in which the neurotrophine functions are involved in defect, particularly of Nerve Growth Factor (NGF), such as neurodegenerative diseases of central nervous system (CNS), acquired immunodeficiency due to a reduced NGF biodisponibility, or morbous conditions in which the stimulus of neoangiogenesis process is convenient.

5 Claims, 7 Drawing Sheets n. 9 (μM)

NGF (nM)

PHARMACEUTICAL COMPOSITIONS FOR THE TREATMENT OF DISEASES RELATED TO NEUROTROPHINES

This application is a U.S. national stage application under 35 U.S.C. §371 of PCT/EP2003/006471, filed Jun. 18, 2003, which claims priority from Italian application number FI2002A000107, filed Jun. 19, 2002.

FIELD OF THE INVENTION

The present invention refers to pharmaceutical compositions comprising 3-aza-bicyclo[3.2.1]octane derivatives of general formula (I), their dimers of general formula (II) or (III) hereinafter reported, or mixtures thereof, useful in the treatment of pathologies in which the neurotrophine functions, particularly of Nerve Growth Factor (NGF), are altered.

STATE OF THE ART

Numerous proteins and polypeptidic factors regulate cell growth and/or survival. The first of such factors which was identified and functionally characterised is NGF. Later on, other proteins belonging to the same NGF family were identified that exert their activity on different populations of nervous cells. All these proteins is are collectively referred to as "neurotrophins".

NGF, upon interaction with specific surface receptors, prevents neuronal cell death during embryonal development and throughout adult life. NGF administration was proven advantageous in pathological conditions, such as degenerative and ischaemic disorders of Central Nervous System (CNS), spinal lesions, and toxicity of excitory amino acids. In fact, together with other neurotrophic factors, NGF promotes neuronal regeneration and supports neuronal functions.

Therapeutic uses of NGF have been limited by its poor ability to get across the blood-brain-barrier, partly due to the molecular size of the native factor. Thus, the development of non-peptidic compounds able to specifically mimic the activities of the natural ligand is a useful approach to obviate such limitations. Relevant examples of such compounds are a) phorbol esters, that mimic NGF presumably by modifying PKCc activity; b) ganglioside and other unrelated lipidic compounds, that promote neuritic outgrowth from dorsal root ganglia, or other sympathetic, neurones; c) Triap (1,1,3-triciano-2-ammino-1-propene), a small compound able to support survival and induce neuritic growth in PC12 cells. In all of the above cases, activity of molecules is not mediated by interactions with NGF receptors. Development of new non-peptidic compounds able to interact with specific receptors, thus behaving as agonists or antagonists, of human neurotrophins is of utmost importance, since they may be used as drugs for treatment of disorders related to a defective or excessive activity of neurotrophins.

SUMMARY OF THE INVENTION

Now, the Applicants have unexpectedly found that 3-aza-bicyclo[3.2.1.]octane derivatives of general formula (I) and their dimers of general formula (II) and (III) as reported hereinafter, are active as agonists of human neurotrophines, therefore they are useful for preparation of pharmaceutical compositions for the treatment of diseases in which the neurotrophine functions, particularly the NGF functions, are involved in defect.

It is therefore subject of the present invention a pharmaceutical composition comprising as the active principle at least one among the 3-aza-bicyclo[3.2.1]octane derivatives of general formula (I), or their dimers of general formula (II) and (III), or mixtures thereof:

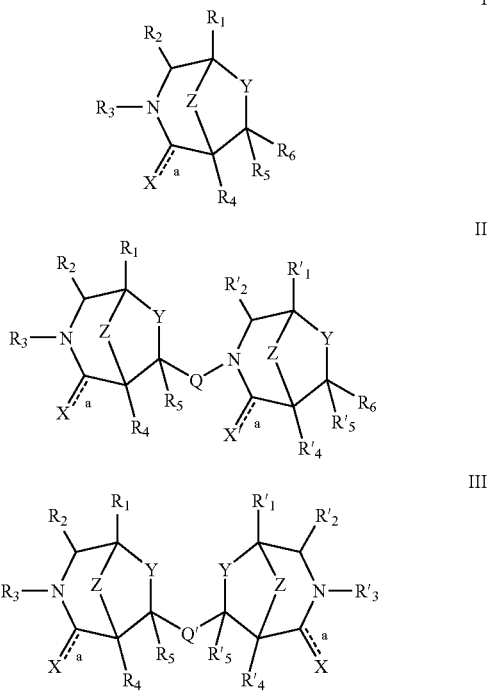

wherein:

$R_1$ and $R'_1$, equal or different between each other, are selected from the group consisting of H, $C_{1-8}$alkyl, $C_{2-8}$alkenyl, $C_{2-8}$alkynyl, cycloalkyl, aryl, heterocycle, aryl$C_{1-8}$alkyl; heterocycle$C_{1-8}$alkyl, RR'N—$C_{1-8}$alkyl, RR'N-aryl, FmocNR'-aryl, BocNR'-aryl, CBzNR'-aryl, RO-aryl, R(O)C-aryl, RO(O)C-aryl, RR'N(O)C-aryl; FmocNR'—$C_{1-8}$alkyl, BocNR'—$C_{1-8}$alkyl, CbzNR'—$C_{1-8}$alkyl, FmocNR'—$C_{1-8}$aryl, BocNR'—$C_{1-8}$aryl and CbzNR'—$C_1$ aryl, $R_2$ and $R'_2$, equal or different between each other, are selected from the group consisting of H, $C_{1-8}$alkyl, $C_{2-8}$alkenyl, $C_{2-8}$alkynyl, cycloalkyl, aryl, aryl$C_{1-8}$alkyl, heterocycle$C_{1-8}$alkyl, amino$C_{1-8}$alkyl, aminoaryl, $C_{1-8}$alkyloxyaryl, hydroxyaryl, hydroxy$C_{1-8}$alkyl, carboxy$C_{1-8}$alkyl, methyloxycarbonyl$C_{1-8}$alkyl, carboxyaryl, carboalkyloxyaryl, alkylcarbamoylaryl and -(side chains of amino acids), or $R_1$ and $R_2$, taken together, and $R_1'$ and $R_2'$, taken together, are $C_{1-4}$alkyl, $C_{2-4}$ alkenyl, cycloalkyl or benzofused cycloalkyl, to form a bridge of 3, 4, 5, 6 terms, $R_3$ and $R_3'$ are selected from the group consisting of H, $C_{1-8}$alkyl, $C_{2-8}$alkenyl, $C_{2-8}$alkynyl, cycloalkyl, aryl, aryl$C_{1-8}$alkyl, heterocycle$C_{1-8}$alkyl, RR'N$C_{1-8}$alkyl, RR'Naryl, RO—$C_{1-8}$alkyl, RO(O)C—$C_{1-8}$alkyl, R(O)C—$C_{1-8}$alkyl, RC(O)O—$C_{1-8}$alkyl, RC(O)N(R)$C_{1-8}$alkyl, RO-aryl, RO(O)C-aryl, R(O)C-aryl RC(O)O-aryl, RC(O)N(R)aryl, —CH(amino acid side-chain)$CO_2R$, —CH(amino acid side-chain)C(O)NR, —CH($CO_2R$)— amino acid side-chain, CH(CONRR')— amino acid side-chain, Fmoc, Boc and Cbz, $R_4$, $R'_4$, $R_5$, and $R'_5$, equal or different amongst each other, are selected from the group consisting of H, $C_{1-8}$alkyl, $C_{2-8}$alchenyl, $C_{2-8}$alchinyl, cycloalkyl, aryl, heterocycle, aryl$C_{1-8}$alkyl and heterocycle$C_{1-8}$alkyl, $R_6$ is selected from the group consisting of H, $C_{1-8}$alkyl, $C_{2-8}$alkenyl, $C_{2-8}$alkynyl, cycloalkyl, aryl, aryl$C_{1-8}$alkyl, heterocycle, heterocycle$C_{1-8}$alkyl; —C(O)R, —C(O)OR, —C(O)NRR', $CH_2$OR, $CH_2$NRR', —C(O)NH—CH(amino acid side-chain)C(O)OR, $CH_2$NR-Fmoc, $CH_2$NR-Boc and $CH_2$NR—CBz, R and R', equal or different between each other, are selected from the group consisting of H, $C_{1-8}$alkyl, $C_{2-8}$alkenyl, $C_{2-8}$alkynyl, cycloalkyl, aryl, heterocycle, aryl$C_{1-8}$alkyl; heterocycle$C_{1-8}$alkyl; protecting group, —C(O)CH-amino acid side-chain)-NHT, —NH—CH(amino acid side-chain)COOT and —CH(amino acid side-chain)COOT, where T is selected from between H and $C_{1-8}$alkyl;

X and X', equal or different between each other, are selected from between O and S, when a is a double bond, or X and X' are both H, when a is a single bond, Y and Z, equal or different from each other, are selected from the group consisting of O, S, SO, $SO_2$ and N—R, wherein R is as above defined;

Q is selected from the group consisting of C=O, $CH_2$, CO—NH—CH (amino acid side-chain)-CO, CONR$(CH_2)_n$CO, CONR—$C_{2-8}$alkenyl-CO C(O)O$(CH_2)_n$CO, $CH_2$OC(O)$(CH_2)_n$CO, and $CH_2$NRC(O)$(CH_2)_n$CO, wherein n is comprised between 2 and 6, and R is as above defined, Q' is selected from the group consisting of C(O)OCH$_2$, C(O)NRCH$_2$, $CH_2$OC(O), $CH_2$NRC(O), CONR$(CH_2)_n$NRCO, —CONR—$C_{2-8}$alkenyl-NRCO, C(O)O$(CH_2)_n$NRCO, CONR$(CH_2)_n$OC(O), $CH_2$OC(O)$(CH_2)_n$OC(O)CH$_2$, $CH_2$NRC(O)$(CH_2)_n$NRC(O)CH$_2$, $CH_2$OC(O)$(CH_2)_n$NRC(O)CH$_2$, $CH_2$NRC(O)$(CH_2)_n$OC(O)CH$_2$, $CH_2$NR$(CH_2)_n$NRCH$_2$, $CH_2$O$(CH_2)_n$OCH$_2$, $CH_2$O$(CH_2)_n$NRCH$_2$, and $CH_2$NR$(CH_2)_n$OCH$_2$, wherein n is comprised between 2 and 6, and R is as above defined, and where the groups alkyl, alkenyl, alkynyl, cycloalkyl, aryl and the heterocyclic groups above reported, are possibly substituted.

Further subject of the invention are the novel 3-aza-bicyclo [3.2.1]octane derivatives of general formula (I) and their dimers of general formula (II) and (III) above reported.

Further subject of the invention is the use of 3-aza-bicyclo [3.2.1]octane derivatives of general formula (I) and their dimers of general formula (II) and (III) above reported for the preparation of pharmaceutical compositions useful for the treatment of:

i) neurodegenerative disorders of the Central Nervous System, such as Alzheimer Disease (AD), Amyotrophic Lateral Sclerosis (ALS), Huntington disease, neuropathies, neural damage caused by hypoxia, ischaemia, or trauma, inducing apoptosis of nervous cells;

ii) acquired immunodeficiency diseases related reduced bioavailability of NGF, such as immunodeficiency of ageing;

iii) diseases in which stimulation of neoangiogenesis turns out to be advantageous, such as myocardial infarction, stroke, or peripheral vasculopathies;

iv) certain pathologies of the eye, such keratitis of diverse aetiology, glaucoma, degenerative or inflammatory conditions of the retina.

Further subject of the invention is the use of 3-aza-bicyclo [3.2.1]octane derivatives of general formula (I), their dimers of general formula (II) or (III) above reported, and mixtures thereof, for the preparation of culture and storage media useful for conservation of explanted corneas destined to transplantation, and the use for promoting in vivo, in vitro, or ex vivo growth and/or survival of neural cells.

Subject of the invention is also the use of 3-aza-bicyclo [3.2.1]octane derivatives of general formula (I), their dimers of general formula (II) or (III) above reported, and mixtures thereof, labelled with suitable reagents (contrast agents, radioisotopes, fluorescent agents etc.), and processed with any procedure useful for medical imaging purposes, for the imaging analysis of tissues and organs containing neurotrophine receptors, either in vitro or in vivo, in particular for monitoring the use and efficacy of drugs, as well as for the diagnosis of mammal diseases in which the neurothrophine receptors are involved.

The characteristic and advantages of the pharmaceutical compositions according the invention will be in detail reported in the following description.

BRIEF DESCRIPTION OF THE DRAWINGS

FIG. 4a shows the displacement curve obtained with the present compound 9 used as competitor. The analysis of data revealed a Kd of 165 nM±0.05.

FIG. 4b shows the displacement curve obtained by using hrNGF as competitor. The analysis of data revealed a Kd of 114 pM±0.01.

DETAILED DESCRIPTION OF THE INVENTION

Figure 1:
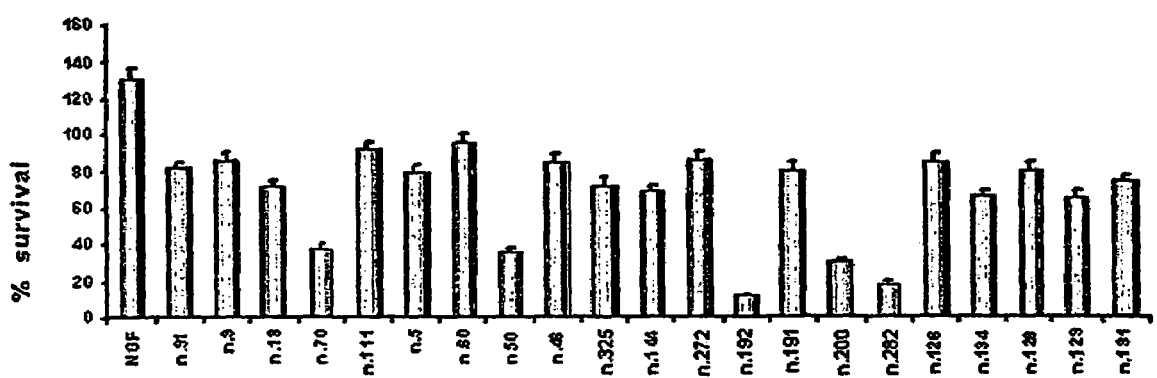
FIG. 1 shows the effect of present compounds on PC12 cell survival in serum-free conditions, by using hrNGF as internal standard, according to paragraph "Biological Activity" hereinafter reported. Results were expressed as survival induced by compounds/spontaneous survival*100 for the compounds indicated on x axis.

In the present invention by the expression "amino acid side chain". It is meant the side chain moieties of the natural occurring L or D amino acids or of the rare or non naturally occurring amino acids.

If it is not otherwise specified, the terms alkyl, alkenyl, alkynyl, aryl, arylalkyl, cycloalkyl and heterocycle, as used in the present invention, should be meant as follows:

$C_{1-8}$alkyl, $C_{2-8}$ alkenyl and $C_{2-8}$ alkynyl relate to linear or branched alkyl radicals, having only single bonds, at least one double bond, at least one triple bond respectively. Examples of alkylic groups according the present invention include but are not limited to, methyl, ethyl, propyl, isopropyl, butyl, pentyl, hexyl, heptyl, octyl. Examples of alkenyl groups, according to the present invention, include but are not limited to ethenyl, propenyl, 1-butenyl, cis-2-butenyl, trans-2-butenyl, 2-methyl-1-propenyl, 1-pentenyl, cis-2-pentenyl, trans-2-pentenyl, 2-methyl-2-butenyl. Examples of alkynyl groups according to the present invention include, but are not limited to, ethynyl, propynyl 1-butynyl, 2-butynyl, 1-pentynyl, 3-methyl-1-butynyl;

by the term "cycloalkyl" a ring containing carbon atom is meant, generally having from 3 to 8 members, and preferably from 5 to 6 members. Examples of cycloalkyl groups include, but are not limited to, cyclopropyl, cyclobutyl, cyclopentyl, cyclohexyl, cycloheptyl, cyclooctyl, norbornanyl, canphanyl, adamantanyl;

the term "aryl" indicates a group containing one or more unsaturated rings, each ring having from 5 to 8 members, preferably 5 or 6 members. Examples of aryl groups include, but are not limited to phenyl, biphenyl and naphtyl;

the term "heterocycle" relates to saturated or aromatic heterocycles containing one or more heteroatoms, and preferably one or more N atoms. Examples of heterocycles include, but are not limited to pyridine, imidazole, pyrrole, indole, triazoles, pyrrolidine, pyperidine;

the term "arylalkyl" indicates a group having an alkyl and an aryl substituent as above defined. As example, arylalkyl includes but is not limited to ethylphenyl, isobutylphenyl, benzyl, ethylbenzyl, propylbenzyl, isopropylbenzyl, butylbenzyl, isobutylbenzyl, cycloexylbenzyl, stirenyl and biphenyl.

In the present invention the groups fluorenylmethoxycarbonyl, t-butyloxycarbonyl, carboxybenzyl, benzyl, phenyl and acetyl are indicated using the common terms Fmoc, Boc, Cbz, Bn, Ph and Ac respectively.

Preferred are the present compounds of formula (I), (II) and (III) wherein Z is O. According to the present invention the alkyl, alkenyl, alkynyl, cycloalkyl, aryl and heterocyclic groups may be substituted with one or more moieties, and preferably one or two moieties chosen from the group consisting of halogen, cyano, nitro, amino, hydroxy, carboxylic acid, carbonyl and $C_{1-6}$ alkyl. The term "halogen" relates to fluorine, chlorine, bromine and iodine.

Among the compounds of general formula (I), (II) and (III) according the invention, the specific compounds reported in the following Tables 1-4 resulted of particular interest for their agonist activity against neurotrophines, and in particular of human NGF; and thus they are the compounds preferably used for the preparation of the pharmaceutical compositions according to the invention.

TABLE 1

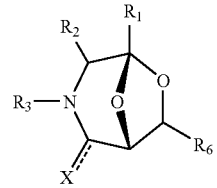

(I)

| Compound | X | $R_1$ | $R_2$ | $R_3$ | $R_6$ |
|---|---|---|---|---|---|
| 1 | O | H | H | PhCH$_2$ | (R) —CO$_2$Me |
| 2 | O | H | H | PhCH$_2$ | (S) —CO$_2$Me |
| 3 | O | H | H | PhCH$_2$ | (R) —CON(CH$_2$)$_5$ |
| 4 | O | H | H | PhCH$_2$ | (R) —CON(CH$_2$)$_4$ |
| 5 | O | H | (S) —Me | PhCH$_2$ | (R) —CO$_2$Me |
| 6 | O | H | (S) —Me | PhCH$_2$ | (S) —CO$_2$Me |
| 7 | O | H | (R) —Me | PhCH$_2$ | (R) —CO$_2$Me |
| 8 | O | H | (R) —Me | PhCH$_2$ | (S) —CO$_2$Me |
| 9 | O | H | (R) —CH$_2$Ph | PhCH$_2$ | (S) —CO$_2$Me |
| 10 | O | H | (R) —CH$_2$Ph | PhCH$_2$ | (R) —CO$_2$Me |
| 11 | O | H | (S) —CH$_2$Ph | PhCH$_2$ | (S) —CO$_2$Me |
| 12 | O | H | (S) —CH$_2$Ph | PhCH$_2$ | (R) —CO$_2$Me |
| 13 | O | H | (S) —CH$_2$OBn | PhCH$_2$ | (R) —CO$_2$Me |
| 14 | O | H | (S) —CH$_2$OBn | PhCH$_2$ | (S) —CO$_2$Me |
| 15 | O | H | (R) —CH$_2$OBn | PhCH$_2$ | (R) —CO$_2$Me |
| 16 | O | H | (R) —CH$_2$OBn | PhCH$_2$ | (S) —CO$_2$Me |
| 17 | O | H | (S) —CH$_2$OH | PhCH$_2$ | (R) —CO$_2$Me |
| 18 | O | H | (S) —CH$_2$OH | PhCH$_2$ | (S) —CO$_2$Me |
| 19 | O | H | (R) —CH$_2$OH | PhCH$_2$ | (R) —CO$_2$Me |
| 20 | O | H | (R) —CH$_2$OH | PhCH$_2$ | (S) —CO$_2$Me |
| 21 | O | H | =CH$_2$ | PhCH$_2$ | (R) —CO$_2$Me |
| 22 | O | H | =CH$_2$ | PhCH$_2$ | (S) —CO$_2$Me |
| 23 | O | H | (R) —CH$_2$OH | PhCH$_2$ | (S) —CO$_2$Me |

TABLE 1-continued (I)

| Compound | X | R₁ | R₂ | R₃ | R₆ |
|---|---|---|---|---|---|
| 24 | S | H | H | PhCH$_2$ | (R)—CO$_2$Me |
| 25 | S | H | H | PhCH$_2$ | (R)—CONH(CH$_2$)$_2$NH$_2$ |
| 26 | S | H | H | PhCH$_2$ | (R)—CONH(CH$_2$)$_2$OH |
| 27 | O | Ph | H | PhCH$_2$ | (R)—CO$_2$Me |
| 28 | O | Ph | H | PhCH$_2$ | (S)—CO$_2$Me |
| 29 | O | Ph | H | CH(Ph)$_2$ | (R)—CO$_2$Me |
| 30 | O | Ph | H | CH(Ph)$_2$ | (S)—CO$_2$Me |
| 31 | O | NO$_2$-Ph | H | Ph | (S)—CO$_2$Me |
| 32 | H | H | H | H | (R)—CO$_2$H |
| 33 | H | H | H | H | (S)—CO$_2$H |
| 34 | H | H | H | H | (R)—CO$_2$Me |
| 35 | H | H | H | H | (S)—CO$_2$Me |
| 36 | H | H | H | PhCH$_2$ | (R)—CO$_2$H |
| 37 | H | H | H | PhCH$_2$ | (S)—CO$_2$H |
| 38 | H | H | H | Fmoc | (R)—CO$_2$H |
| 39 | H | H | H | Fmoc | (S)—CO$_2$H |
| 40 | H | H | H | PhCH$_2$ | (R)—CO$_2$Me |
| 41 | H | H | H | PhCH$_2$ | (S)—CO$_2$Me |
| 42 | H | H | H | Boc | (R)—CO$_2$Me |
| 43 | H | H | H | Boc | (S)—CO$_2$Me |
| 44 | H | H | H | Fmoc | (R)—CO$_2$Me |
| 45 | H | H | H | Fmoc | (S)—CO$_2$Me |
| 46 | H | H | H | H | (R)—CONHMe |
| 47 | H | H | H | H | (S)—CONHMe |
| 48 | H | H | H | Ac | (R)—CONHMe |
| 49 | H | H | H | Ac | (S)—CONHMe |
| 50 | H | H | H | PhCH$_2$ | (R)—CONHMe |
| 51 | H | H | H | PhCH$_2$ | (S)—CONHMe |
| 52 | H | H | H | Fmoc | (R)—CONHMe |
| 53 | H | H | H | Fmoc | (S)—CONHMe |
| 54 | H | H | H | PhCH$_2$ | (R)—CON(CH$_2$)$_5$ |
| 55 | H | H | H | PhCH$_2$ | (R)—CONHcyclohexyl |
| 56 | H | H | H | PhCH$_2$ | (R)—CON(CH$_2$)$_4$ |
| 57 | H | H | H | PhCH$_2$ | (R)—CONH(CH$_2$)$_2$OH |
| 58 | H | H | H | H | (R)—CH$_2$OH |
| 59 | H | H | H | H | (S)—CH$_2$OH |
| 60 | H | H | H | Fmoc | (S)—CH$_2$OH |
| 61 | H | H | H | Fmoc | (R)—CH$_2$OH |
| 62 | H | H | H | Boc | (R)—CH$_2$OH |
| 63 | H | H | H | Boc | (S)—CH$_2$OH |
| 64 | H | H | H | PhCH$_2$ | (R)—CH$_2$OH |
| 65 | H | H | H | PhCH$_2$ | (S)—CH$_2$OH |
| 66 | H | H | (S)—CH$_2$OBn | PhCH$_2$ | (R)—CO$_2$Me |
| 67 | H | H | (S)—CH$_2$OBn | PhCH$_2$ | (S)—CO$_2$Me |
| 68 | H | H | (R)—CH$_2$OBn | PhCH$_2$ | (R)—CO$_2$Me |
| 69 | H | H | (R)—CH$_2$OBn | PhCH$_2$ | (S)—CO$_2$Me |
| 70 | H | H | (S)—CH$_2$OBn | PhCH$_2$ | (R)—CH$_2$OH |
| 71 | H | H | (S)—CH$_2$OBn | PhCH$_2$ | (S)—CH$_2$OH |
| 72 | H | H | (R)—CH$_2$OBn | PhCH$_2$ | (R)—CH$_2$OH |
| 73 | H | H | (R)—CH$_2$OBn | PhCH$_2$ | (S)—CO$_2$Me |
| 75 | H | H | (S)—COOH | Fmoc | (R)—CO$_2$Me |
| 76 | H | H | (S)—COOH | Fmoc | (S)—CO$_2$Me |
| 77 | H | H | (R)—COOH | Fmoc | (R)—CO$_2$Me |
| 78 | H | H | (R)—COOH | Fmoc | (S)—CO$_2$Me |
| 79 | H | H | (S)—CH$_2$OBn | Fmoc | (R)—CO$_2$Me |
| 80 | H | H | (S)—CH$_2$OBn | Fmoc | (S)—CO$_2$Me |
| 81 | H | H | (R)—CH$_2$OBn | Fmoc | (R)—CO$_2$Me |
| 82 | H | H | (R)—CH$_2$OBn | Fmoc | (S)—CO$_2$Me |
| 83 | H | H | (S)—CH$_2$OBn | H | (R)—CO$_2$Me |
| 84 | H | H | (S)—CH$_2$OBn | H | (S)—CO$_2$Me |
| 85 | H | H | (R)—CH$_2$OBn | H | (R)—CO$_2$Me |
| 86 | H | H | (R)—CH$_2$OBn | H | (S)—CO$_2$Me |
| 87 | H | H | (S)—CH$_2$OH | H | (R)—CO$_2$Me |
| 88 | H | H | (S)—CH$_2$OH | H | (S)—CO$_2$Me |
| 89 | H | H | (R)—CH$_2$OH | H | (R)—CO$_2$Me |
| 90 | H | H | (R)—CH$_2$OH | H | (S)—CO$_2$Me |

TABLE 1-continued

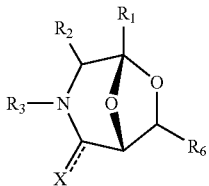

(I)

| Compound | X | R₁ | R₂ | R₃ | R₆ |
|---|---|---|---|---|---|
| 91 | H | H | (S) —CH₂OH | Fmoc | (R) —CO₂Me |
| 92 | H | H | (S) —CH₂OH | Fmoc | (S) —CO₂Me |
| 93 | H | H | (R) —CH₂OH | Fmoc | (R) —CO₂Me |
| 94 | H | H | (R) —CH₂OH | Fmoc | (S) —CO₂Me |
| 95 | H | H | (S) —CH₂OH | Fmoc | (R) —CO₂Me |
| 96 | H | H | (S) —CH₂OH | Fmoc | (S) —CO₂Me |
| 97 | H | H | (R) —CH₂OH | Fmoc | (R) —CO₂Me |
| 98 | H | H | (R) —CH₂OH | Fmoc | (S) —CO₂Me |
| 99 | H | H | (S) —CH₂OH | PhCH₂ | (S) —CO₂Me |
| 100 | H | H | (R) —CH₂OH | PhCH₂ | (R) —CO₂Me |
| 101 | H | H | (R) —CH₂OH | PhCH₂ | (R) —CO₂Me |
| 102 | H | H | (R) —CH₂OH | PhCH₂ | (S) —CO₂Me |
| 103 | H | H | (S) —CH₂OH | Fmoc | (R) —CO₂OH |
| 104 | H | H | (S) —CH₂OH | Fmoc | (S) —CO₂OH |
| 105 | H | H | (R) —CH₂OH | Fmoc | (R) —CO₂OH |
| 106 | H | H | (R) —CH₂OH | Fmoc | (S) —CO₂OH |
| 107 | H | H | (S) —CH₂OH | PhCH₂ | (R) —CO₂OH |
| 108 | H | H | (S) —CH₂OH | PhCH₂ | (S) —CO₂OH |
| 109 | H | H | (R) —CH₂OH | PhCH₂ | (R) —CO₂OH |
| 110 | H | H | (R) —CH₂OH | PhCH₂ | (S) —CO₂OH |
| 111 | H | H | =CH₂ | PhCH₂ | (R) —CO₂Me |
| 112 | H | H | =CH₂ | PhCH₂ | (S) —CO₂Me |
| 113 | H | H | =CH₂ | PhCH₂ | (R) —CH₂OH |
| 114 | H | H | =CH₂ | PhCH₂ | (S) —CH₂OH |
| 115 | H | H | (S) —CH₂CH(Me)₂ | Fmoc | (R) —CH₂OH |
| 116 | H | H | (S) —CH₂CH(Me)₂ | PhCH₂ | (S) —CH₂OH |
| 117 | H | H | (S) —CH₂CH(Me)₂ | H | (R) —CH₂OH |
| 118 | H | Ph | H | H | (R) —CO₂Me |
| 119 | H | Ph | H | Fmoc | (R) —CO₂Me |
| 120 | H | Ph | H | PhCH₂ | (R) —CO₂Me |
| 121 | H | Ph | H | CH(Ph)₂ | (R) —CO₂Me |
| 122 | H | Ph | H | H | (S) —CO₂Me |
| 123 | H | Ph | H | Fmoc | (S) —CO₂Me |
| 124 | H | Ph | H | PhCH₂ | (S) —CO₂Me |
| 125 | H | Ph | H | CH(Ph)₂ | (S) —CO₂Me |
| 126 | H | p-NH₂—C₆H₄ | H | Ph | (S) —COOMe |
| 127 | H | p-NH₂—C₆H₄ | H | Ph | (S) —COOH |
| 128 | H | p-NH₂—C₆H₄ | H | Ph | (S) —CONHCH₂CO₂Me |
| 129 | H | p-NH—(Asp(OᵗBu)—NH₂) C₆H₄ | H | Ph | (S) —CO₂Me |
| 130 | H | p-NH—(Asp(OᵗBu)—NH₂)—C₆H₄ | H | Ph | (S) —CO₂H |
| 131 | H | p-NH—(Asp(OᵗBu)—NH₂) C₆H₄ | H | Ph | (S) —CONH—Lys(NHBoc)—OMe |
| 132 | H | p-NH—(Asp(OH)—NH₂)—C₆H₄ | H | Ph | (S) —CONH—Lys—OMe |
| 133 | H | p-NO₂—C₆H₄ | H | Ph | (S) —COOH |
| 134 | H | p-NO₂—C₆H₄ | H | Ph | (S) —COOMe |
| 135 | H | p-NO₂—C₆H₄ | H | Ph | (S) —CONHCH₂CO₂Me |
| 136 | H | Ph | H | H | (R) —CH₂OH |
| 137 | H | Ph | H | Fmoc | (R) —CH₂OH |
| 138 | H | Ph | H | PhCH₂ | (R) —CH₂OH |
| 139 | H | Ph | H | CH(Ph)₂ | (R) —CH₂OH |
| 140 | H | Ph | H | H | (S) —CH₂OH |
| 141 | H | Ph | H | Fmoc | (S) —CH₂OH |
| 142 | H | Ph | H | PhCH₂ | (S) —CH₂OH |
| 143 | H | Ph | H | CH(Ph)₂ | (S) —CH₂OH |
| 144 | H | H | (S) —Me | Fmoc | (R) —CO₂OH |
| 145 | H | H | (S) —Me | Fmoc | (S) —CO₂OH |
| 146 | H | H | (R) —Me | Fmoc | (R) —CO₂OH |
| 147 | H | H | (R) —Me | Fmoc | (S) —CO₂OH |
| 148 | H | H | (S) —Me | Fmoc | (R) —CO₂Me |
| 149 | H | H | (S) —Me | Fmoc | (S) —CO₂Me |
| 150 | H | H | (R) —Me | Fmoc | (R) —CO₂Me |
| 151 | H | H | (R) —Me | Fmoc | (S) —CO₂Me |
| 152 | H | H | (S) —Me | PhCH₂ | (R) —CO₂Me |

TABLE 1-continued (I)

| Compound | X | $R_1$ | $R_2$ | $R_3$ | $R_6$ |
|---|---|---|---|---|---|
| 153 | H | H | (S)—Me | PhCH$_2$ | (S)—CO$_2$Me |
| 154 | H | H | (R)—Me | PhCH$_2$ | (R)—CO$_2$Me |
| 155 | H | H | (R)—Me | PhCH$_2$ | (S)—CO$_2$Me |
| 156 | H | H | (S)—Me | Fmoc | (R)—CH$_2$OH |
| 157 | H | H | (S)—Me | Fmoc | (S)—CH$_2$OH |
| 158 | H | H | (R)—Me | Fmoc | (R)—CH$_2$OH |
| 159 | H | H | (R)—Me | Fmoc | (S)—CH$_2$OH |
| 160 | H | H | (S)—Me | PhCH$_2$ | (R)—CH$_2$OH |
| 161 | H | H | (S)—Me | PhCH$_2$ | (S)—CH$_2$OH |
| 162 | H | H | (R)—Me | PhCH$_2$ | (R)—CH$_2$OH |
| 163 | H | H | (R)—Me | PhCH$_2$ | (S)—CH$_2$OH |
| 164 | H | H | (S)—PhCH$_2$ | Fmoc | (R)—CO$_2$H |
| 165 | H | H | (S)—PhCH$_2$ | Fmoc | (S)—CO$_2$H |
| 166 | H | H | (R)—PhCH$_2$ | Fmoc | (R)—CO$_2$H |
| 167 | H | H | (R)—PhCH$_2$ | Fmoc | (S)—CO$_2$H |
| 168 | H | H | (S)—PhCH$_2$ | Fmoc | (R)—CO$_2$Me |
| 169 | H | H | (S)—PhCH$_2$ | Fmoc | (S)—CO$_2$Me |
| 170 | H | H | (R)—PhCH$_2$ | Fmoc | (R)—CO$_2$Me |
| 171 | H | H | (R)—PhCH$_2$ | Fmoc | (S)—CO$_2$Me |
| 172 | H | H | (S)—PhCH$_2$ | PhCH$_2$ | (R)—CO$_2$Me |
| 173 | H | H | (S)—PhCH$_2$ | PhCH$_2$ | (S)—CO$_2$Me |
| 174 | H | H | (R)—PhCH$_2$ | PhCH$_2$ | (R)—CO$_2$Me |
| 175 | H | H | (R)—PhCH$_2$ | PhCH$_2$ | (S)—CO$_2$Me |
| 176 | H | H | (R)—PhCH$_2$ | H | (R)—CO$_2$Me |
| 177 | H | H | (R)—PhCH$_2$ | H | (S)—CO$_2$Me |
| 178 | H | H | (S)—PhCH$_2$ | H | (R)—CO$_2$Me |
| 179 | H | H | (S)—PhCH$_2$ | H | (S)—CO$_2$Me |
| 180 | H | H | (S)—PhCH$_2$ | Fmoc | (R)—CH$_2$OH |
| 181 | H | H | (S)—PhCH$_2$ | Fmoc | (S)—CH$_2$OH |
| 182 | H | H | (R)—PhCH$_2$ | Fmoc | (R)—CH$_2$OH |
| 183 | H | H | (R)—PhCH$_2$ | Fmoc | (S)—CH$_2$OH |
| 184 | H | H | (S)—PhCH$_2$ | PhCH$_2$ | (R)—CH$_2$OH |
| 185 | H | H | (S)—PhCH$_2$ | PhCH$_2$ | (S)—CH$_2$OH |
| 186 | H | H | (R)—PhCH$_2$ | PhCH$_2$ | (R)—CH$_2$OH |
| 187 | H | H | (R)—PhCH$_2$ | PhCH$_2$ | (S)—CH$_2$OH |
| 188 | H | H | (S)—PhCH$_2$ | PhCH$_2$ | (R)—COOH |
| 189 | O | p-NO$_2$Ph | H | Ph | (R)—CONH(CH$_2$)$_6$NH$_2$ |

TABLE 2

(I)

| Compound | X | $R_1$ | $R_2$ | $R_3$ | $R_6$ |
|---|---|---|---|---|---|
| 190 | O | H | H | PhCH$_2$ | (R)—CO$_2$Me |
| 191 | O | H | H | PhCH$_2$ | (S)—CO$_2$Me |
| 192 | O | H | (S)—Me | PhCH$_2$ | (R)—CO$_2$Me |
| 193 | O | H | (S)—Me | PhCH$_2$ | (S)—CO$_2$Me |
| 194 | O | H | (R)—Me | PhCH$_2$ | (R)—CO$_2$Me |
| 195 | O | H | (R)—Me | PhCH$_2$ | (S)—CO$_2$Me |
| 196 | O | H | (S)—PhCH$_2$ | PhCH$_2$ | (R)—CO$_2$Me |
| 197 | O | H | (S)—PhCH$_2$ | PhCH$_2$ | (S)—CO$_2$Me |
| 198 | O | H | (R)—PhCH$_2$ | PhCH$_2$ | (R)—CO$_2$Me |
| 199 | O | H | (R)—PhCH$_2$ | PhCH$_2$ | (S)—CO$_2$Me |
| 200 | O | H | (S)—CH$_2$CH(Me)$_2$ | PhCH$_2$ | (R)—CO$_2$Me |
| 201 | O | H | (S)—CH$_2$CH(Me)$_2$ | PhCH$_2$ | (S)—CO$_2$Me |
| 202 | O | H | (R)—CH$_2$CH(Me)$_2$ | PhCH$_2$ | (R)—CO$_2$Me |
| 203 | O | H | (R)—CH$_2$CH(Me)$_2$ | PhCH$_2$ | (S)—CO$_2$Me |
| 204 | O | H | H | PhCH$_2$ | (R)—CONHMe |
| 205 | O | H | H | PhCH$_2$ | (S)—CONHMe |
| 206 | O | H | (S)—Me | PhCH$_2$ | (R)—CONHMe |
| 207 | O | H | (S)—Me | PhCH$_2$ | (S)—CONHMe |
| 208 | O | H | (R)—Me | PhCH$_2$ | (R)—CONHMe |
| 209 | O | H | (R)—Me | PhCH$_2$ | (S)—CONHMe |
| 210 | O | H | (S)—PhCH$_2$ | PhCH$_2$ | (R)—CONHMe |
| 211 | O | H | (S)—PhCH$_2$ | PhCH$_2$ | (S)—CONHMe |

TABLE 2-continued (I)

| Compound | X | R₁ | R₂ | R₃ | R₆ |
|---|---|---|---|---|---|
| 212 | O | H | (R)—PhCH₂ | PhCH₂ | (R)—CONHMe |
| 213 | O | H | (R)—PhCH₂ | PhCH₂ | (S)—CONHMe |
| 214 | O | H | (S)—CH₂CH(Me)₂ | PhCH₂ | (R)—CONHMe |
| 215 | O | H | (S)—CH₂CH(Me)₂ | PhCH₂ | (S)—CONHMe |
| 216 | O | H | (R)—CH₂CH(Me)₂ | PhCH₂ | (R)—CONHMe |
| 217 | O | H | (R)—CH₂CH(Me)₂ | PhCH₂ | (S)—CONHMe |
| 218 | H | H | H | Fmoc | (R)—CO₂H |
| 219 | H | H | H | Fmoc | (R)—CO₂Me |
| 220 | H | H | H | Fmoc | (S)—CO₂H |
| 221 | H | H | H | Fmoc | (S)—CO₂Me |
| 222 | H | H | (S)—Me | Fmoc | (R)—CO₂H |
| 223 | H | H | (S)—Me | Fmoc | (R)—CO₂Me |
| 224 | H | H | (S)—Me | PhCH₂ | (R)—CO₂Me |
| 225 | H | H | (R)—Me | Fmoc | (R)—CO₂H |
| 226 | H | H | (R)—Me | Fmoc | (R)—CO₂Me |
| 227 | H | H | (R)—Me | PhCH₂ | (R)—CO₂Me |
| 228 | H | H | (S)—Me | Fmoc | (S)—CO₂H |
| 229 | H | H | (S)—Me | Fmoc | (S)—CO₂Me |
| 230 | H | H | (S)—Me | PhCH₂ | (S)—CO₂Me |
| 231 | H | H | (R)—Me | Fmoc | (S)—CO₂H |
| 232 | H | H | (R)—Me | Fmoc | (S)—CO₂Me |
| 233 | H | H | (R)—Me | PhCH₂ | (S)—CO₂Me |
| 234 | H | H | (S)—PhCH₂ | Fmoc | (R)—CO₂H |
| 235 | H | H | (S)—PhCH₂ | Fmoc | (R)—CO₂Me |
| 236 | H | H | (S)—PhCH₂ | PhCH₂ | (R)—CO₂Me |
| 237 | H | H | (R)—PhCH₂ | Fmoc | (R)—CO₂H |
| 238 | H | H | (R)—PhCH₂ | Fmoc | (R)—CO₂Me |
| 239 | H | H | (R)—PhCH₂ | PhCH₂ | (R)—CO₂Me |
| 240 | H | H | (S)—PhCH₂ | Fmoc | (S)—CO₂H |
| 241 | H | H | (S)—PhCH₂ | Fmoc | (S)—CO₂Me |
| 242 | H | H | (S)—PhCH₂ | PhCH₂ | (S)—CO₂Me |
| 243 | H | H | (R)—PhCH₂ | Fmoc | (S)—CO₂H |
| 244 | H | H | (R)—PhCH₂ | Fmoc | (S)—CO₂Me |
| 245 | H | H | (R)—PhCH₂ | PhCH₂ | (S)—CO₂Me |
| 246 | H | H | (R)—CH₂OH | Fmoc | (S)—CO₂Me |
| 247 | H | H | (R)—CH₂OH | PhCH₂ | (S)—CO₂Me |
| 248 | H | H | (R)—CH₂OBn | Fmoc | (S)—CO₂Me |
| 249 | H | H | (R)—CH₂OBn | PhCH₂ | (S)—CO₂Me |
| 250 | H | H | (R)—CH₂OH | Fmoc | (R)—CO₂Me |
| 251 | H | H | (R)—CH₂OH | PhCH₂ | (R)—CO₂Me |
| 252 | H | H | (R)—CH₂OBn | Fmoc | (R)—CO₂Me |
| 253 | H | H | (R)—CH₂OBn | PhCH₂ | (R)—CO₂Me |
| 254 | H | H | (S)—CH₂OH | Fmoc | (R)—CO₂Me |
| 255 | H | H | (S)—CH₂OH | PhCH₂ | (R)—CO₂Me |
| 256 | H | H | (S)—CH₂OBn | Fmoc | (R)—CO₂Me |
| 257 | H | H | (S)—CH₂OBn | PhCH₂ | (R)—CO₂Me |
| 258 | H | H | (S)—CH₂OH | Fmoc | (R)—CO₂Me |
| 259 | H | H | (S)—CH₂OH | PhCH₂ | (R)—CO₂Me |
| 260 | H | H | (S)—CH₂OBn | Fmoc | (R)—CO₂Me |
| 261 | H | H | (S)—CH₂OBn | PhCH₂ | (R)—CO₂Me |
| 262 | H | H | (S)—CH₂CH(Me)₂ | Bn | (R)—CO₂Me |
| 263 | H | H | (R)—CH₂CH(Me)₂ | Bn | (R)—CO₂Me |
| 264 | H | H | (S)—CH₂CH(Me)₂ | Bn | (S)—CO₂Me |
| 265 | H | H | (R)—CH₂CH(Me)₂ | Bn | (S)—CO₂Me |
| 266 | H | H | (S)—CH₂CH(Me)₂ | Fmoc | (R)—CO₂Me |
| 267 | H | H | (R)—CH₂CH(Me)₂ | Fmoc | (R)—CO₂Me |
| 268 | H | H | (S)—CH₂CH(Me)₂ | Fmoc | (S)—CO₂Me |
| 269 | H | H | (R)—CH₂CH(Me)₂ | Fmoc | (S)—CO₂Me |
| 270 | H | H | (S)—Me | H | (R)—CH₂OH |
| 271 | H | H | (S)—Me | Bn | (R)—CH₂OH |
| 272 | H | H | (S)—Me | Fmoc | (R)—CH₂OH |
| 273 | H | H | (R)—Me | H | (R)—CH₂OH |
| 274 | H | H | (R)—Me | Bn | (R)—CH₂OH |
| 275 | H | H | (R)—Me | Fmoc | (R)—CH₂OH |
| 276 | H | H | (S)—Me | H | (S)—CH₂OH |
| 277 | H | H | (S)—Me | Bn | (S)—CH₂OH |
| 278 | H | H | (S)—Me | Fmoc | (S)—CH₂OH |
| 279 | H | H | (R)—Me | H | (S)—CH₂OH |
| 280 | H | H | (R)—Me | Bn | (S)—CH₂OH |
| 281 | H | H | (R)—Me | Fmoc | (S)—CH₂OH |
| 282 | H | H | (S)—CH₂CH(Me)₂ | H | (R)—CH₂OH |
| 283 | H | H | (S)—CH₂CH(Me)₂ | Bn | (R)—CH₂OH |
| 284 | H | H | (S)—CH₂CH(Me)₂ | Fmoc | (R)—CH₂OH |
| 285 | H | H | (R)—CH₂CH(Me)₂ | H | (R)—CH₂OH |
| 286 | H | H | (R)—CH₂CH(Me)₂ | Bn | (R)—CH₂OH |
| 287 | H | H | (R)—CH₂CH(Me)₂ | Fmoc | (R)—CH₂OH |
| 288 | H | H | (S)—CH₂CH(Me)₂ | H | (S)—CH₂OH |
| 289 | H | H | (S)—CH₂CH(Me)₂ | Bn | (S)—CH₂OH |
| 290 | H | H | (S)—CH₂CH(Me)₂ | Fmoc | (S)—CH₂OH |
| 291 | H | H | (R)—CH₂CH(Me)₂ | H | (S)—CH₂OH |
| 292 | H | H | (R)—CH₂CH(Me)₂ | Bn | (S)—CH₂OH |
| 293 | H | H | (R)—CH₂CH(Me)₂ | Fmoc | (S)—CH₂OH |
| 294 | H | H | (S)—PhCH₂ | H | (R)—CH₂OH |
| 295 | H | H | (S)—PhCH₂ | Bn | (R)—CH₂OH |
| 296 | H | H | (S)—PhCH₂ | Fmoc | (R)—CH₂OH |
| 297 | H | H | (R)—PhCH₂ | H | (R)—CH₂OH |
| 298 | H | H | (R)—PhCH₂ | Bn | (R)—CH₂OH |
| 299 | H | H | (R)—PhCH₂ | Fmoc | (R)—CH₂OH |
| 300 | H | H | (S)—PhCH₂ | H | (S)—CH₂OH |
| 301 | H | H | (S)—PhCH₂ | Bn | (S)—CH₂OH |
| 302 | H | H | (S)—PhCH₂ | Fmoc | (S)—CH₂OH |
| 303 | H | H | (R)—PhCH₂ | H | (S)—CH₂OH |
| 304 | H | H | (R)—PhCH₂ | Bn | (S)—CH₂OH |
| 305 | H | H | (R)—PhCH₂ | Fmoc | (S)—CH₂OH |
| 306 | H | H | (R)—CH₂OH | Fmoc | (S)—CH₂OH |
| 307 | H | H | (R)—CH₂OH | PhCH₂ | (S)—CH₂OH |
| 308 | H | H | (R)—CH₂OBn | Fmoc | (S)—CH₂OH |
| 309 | H | H | (R)—CH₂OBn | PhCH₂ | (S)—CH₂OH |
| 310 | H | H | (R)—CH₂OH | Fmoc | (R)—CH₂OH |
| 311 | H | H | (R)—CH₂OH | PhCH₂ | (R)—CH₂OH |
| 312 | H | H | (R)—CH₂OBn | Fmoc | (R)—CH₂OH |
| 313 | H | H | (R)—CH₂OBn | PhCH₂ | (R)—CH₂OH |
| 314 | H | H | (S)—CH₂OH | Fmoc | (S)—CH₂OH |
| 315 | H | H | (S)—CH₂OH | PhCH₂ | (S)—CH₂OH |
| 316 | H | H | (S)—CH₂OBn | Fmoc | (S)—CH₂OH |
| 317 | H | H | (S)—CH₂OBn | PhCH₂ | (S)—CH₂OH |
| 318 | H | H | (S)—CH₂OH | Fmoc | (R)—CH₂OH |
| 319 | H | H | (S)—CH₂OH | PhCH₂ | (R)—CH₂OH |
| 320 | H | H | (S)—CH₂OBn | Fmoc | (R)—CH₂OH |
| 321 | H | H | (S)—CH₂OBn | PhCH₂ | (R)—CH₂OH |

TABLE 3

(II)

| Compound | R₁ | R₂ | R₃ | R'₁ | R'₂ | R₆ |
|---|---|---|---|---|---|---|
| 322 | H | H | H | H | H | CO₂Me |
| 323 | H | H | H | H | H | CONHMe |
| 324 | H | H | PhCH₂ | H | H | CO₂Me |
| 325 | H | H | PhCH₂ | H | H | CONHMe |
| 326 | H | H | Fmoc | H | H | CO₂Me |

TABLE 3-continued (II)

| Compound | R₁ | R₂ | R₃ | R'₁ | R'₂ | R₆ |
|---|---|---|---|---|---|---|
| 327 | H | H | Fmoc | H | H | CONHMe |
| 328 | H | H | Boc | H | H | CO₂Me |
| 329 | H | H | Boc | H | H | CONHMe |
| 330 | H | PhCH₂ | H | H | H | CO₂Me |
| 331 | H | PhCH₂ | H | H | H | CONHMe |
| 332 | H | PhCH₂ | PhCH₂ | H | H | CO₂Me |
| 333 | H | PhCH₂ | PhCH₂ | H | H | CONHMe |
| 334 | H | PhCH₂ | Fmoc | H | H | CO₂Me |
| 335 | H | PhCH₂ | Fmoc | H | H | CONHMe |
| 336 | H | PhCH₂ | Boc | H | H | CO₂Me |
| 337 | H | PhCH₂ | Boc | H | H | CONHMe |
| 338 | H | H | H | H | PhCH₂ | CO₂Me |
| 339 | H | H | H | H | PhCH₂ | CONHMe |
| 340 | H | H | PhCH₂ | H | PhCH₂ | CO₂Me |
| 341 | H | H | PhCH₂ | H | PhCH₂ | CONHMe |
| 342 | H | H | Fmoc | H | PhCH₂ | CO₂Me |
| 343 | H | H | Fmoc | H | PhCH₂ | CONHMe |
| 344 | H | H | Boc | H | PhCH₂ | CO₂Me |
| 345 | H | H | Boc | H | PhCH₂ | CONHMe |
| 346 | H | PhCH₂ | H | H | PhCH₂ | CO₂Me |
| 347 | H | PhCH₂ | H | H | PhCH₂ | CONHMe |
| 348 | H | PhCH₂ | PhCH₂ | H | PhCH₂ | CO₂Me |
| 349 | H | PhCH₂ | PhCH₂ | H | PhCH₂ | CONHMe |
| 350 | H | PhCH₂ | Fmoc | H | PhCH₂ | CO₂Me |
| 351 | H | PhCH₂ | Fmoc | H | PhCH₂ | CONHMe |
| 352 | H | PhCH₂ | Boc | H | PhCH₂ | CO₂Me |
| 353 | H | PhCH₂ | Boc | H | PhCH₂ | CONHMe |
| 354 | Ph | H | H | H | H | CO₂Me |
| 355 | Ph | H | H | H | H | CONHMe |
| 356 | Ph | H | PhCH₂ | H | H | CO₂Me |
| 357 | Ph | H | PhCH₂ | H | H | CONHMe |
| 358 | Ph | H | Fmoc | H | H | CO₂Me |
| 359 | Ph | H | Fmoc | H | H | CONHMe |
| 360 | Ph | H | Boc | H | H | CO₂Me |
| 361 | Ph | H | Boc | H | H | CONHMe |
| 362 | H | H | H | Ph | H | CO₂Me |
| 363 | H | H | H | Ph | H | CONHMe |
| 364 | H | H | PhCH₂ | Ph | H | CO₂Me |
| 365 | H | H | PhCH₂ | Ph | H | CONHMe |
| 366 | H | H | Fmoc | Ph | H | CO₂Me |
| 367 | H | H | Fmoc | Ph | H | CONHMe |
| 368 | H | H | Boc | Ph | H | CO₂Me |
| 369 | H | H | Boc | Ph | H | CONHMe |
| 370 | Ph | H | H | Ph | H | CO₂Me |
| 371 | Ph | H | H | Ph | H | CONHMe |
| 372 | Ph | H | PhCH₂ | Ph | H | CO₂Me |
| 373 | Ph | H | PhCH₂ | Ph | H | CONHMe |
| 374 | Ph | H | Fmoc | Ph | H | CO₂Me |
| 375 | Ph | H | Fmoc | Ph | H | CONHMe |
| 376 | Ph | H | Boc | Ph | H | CO₂Me |
| 377 | Ph | H | Boc | Ph | H | CONHMe |
| 378 | H | H | H | H | CH₂OH | CO₂Me |
| 379 | H | H | H | H | CH₂OH | CONHMe |
| 380 | H | H | PhCH₂ | H | CH₂OH | CO₂Me |
| 381 | H | H | PhCH₂ | H | CH₂OH | CONHMe |
| 382 | H | H | Fmoc | H | CH₂OH | CO₂Me |
| 383 | H | H | Fmoc | H | CH₂OH | CONHMe |
| 384 | H | H | Boc | H | CH₂OH | CO₂Me |
| 385 | H | H | Boc | H | CH₂OH | CONHMe |
| 386 | H | PhCH₂ | H | H | CH₂OH | CO₂Me |
| 387 | H | PhCH₂ | H | H | CH₂OH | CONHMe |
| 388 | H | PhCH₂ | PhCH₂ | H | CH₂OH | CO₂Me |
| 389 | H | PhCH₂ | PhCH₂ | H | CH₂OH | CONHMe |
| 390 | H | PhCH₂ | Fmoc | H | CH₂OH | CO₂Me |
| 391 | H | PhCH₂ | Fmoc | H | CH₂OH | CONHMe |
| 392 | H | PhCH₂ | Boc | H | CH₂OH | CO₂Me |
| 393 | H | PhCH₂ | Boc | H | CH₂OH | CONHMe |
| 394 | Ph | H | H | H | CH₂OH | CO₂Me |
| 395 | Ph | H | H | H | CH₂OH | CONHMe |
| 396 | Ph | H | PhCH₂ | H | CH₂OH | CO₂Me |
| 397 | Ph | H | PhCH₂ | H | CH₂OH | CONHMe |
| 398 | Ph | H | Fmoc | H | CH₂OH | CO₂Me |
| 399 | Ph | H | Fmoc | H | CH₂OH | CONHMe |
| 400 | Ph | H | Boc | H | CH₂OH | CO₂Me |
| 401 | Ph | H | Boc | H | CH₂OH | CONHMe |

TABLE 4

(III)

| Compound | R₁ | R₂ | R₃ | R'₁ | R'₂ | R'₃ | X | Q' |
|---|---|---|---|---|---|---|---|---|
| 402 | H | H | H | H | H | H | O | CO—NH(CH₂)₂NH—CO |
| 403 | H | H | H | H | H | H | O | CO—NH(CH₂)₄NH—CO |
| 404 | H | H | H | H | H | H | O | CO—NH(CH₂)₆NH—CO |
| 405 | H | H | H | H | H | H | O | CO—N(C₂H₄)N—CO |
| 406 | H | H | PhCH₂ | H | H | PhCH₂ | O | CO—NH(CH₂)₂NH—CO |
| 407 | H | H | PhCH₂ | H | H | PhCH₂ | O | CO—NH(CH₂)₄NH—CO |
| 408 | H | H | PhCH₂ | H | H | PhCH₂ | O | CO—NH(CH₂)₆NH—CO |
| 409 | H | H | PhCH₂ | H | H | PhCH₂ | O | CO—N(C₂H₄)N—CO |
| 410 | H | H | PhCH₂ | H | H | PhCH₂ | H | CO—NH(CH₂)₂NH—CO |

TABLE 4-continued (III)

| Compound | $R_1$ | $R_2$ | $R_3$ | $R'_1$ | $R'_2$ | $R'_3$ | X | Q' |
|---|---|---|---|---|---|---|---|---|
| 411 | H | H | $PhCH_2$ | H | H | $PhCH_2$ | H | $CO-NH(CH_2)_4NH-CO$ |
| 412 | H | H | $PhCH_2$ | H | H | $PhCH_2$ | H | $CO-NH(CH_2)_6NH-CO$ |
| 413 | H | H | $PhCH_2$ | H | H | $PhCH_2$ | H | $CO-N(C_2H_4)N-CO$ |
| 414 | H | $PhCH_2$ | $PhCH_2$ | H | $PhCH_2$ | $PhCH_2$ | O | $CO-NH(CH_2)_2NH-CO$ |
| 415 | H | $PhCH_2$ | $PhCH_2$ | H | $PhCH_2$ | $PhCH_2$ | O | $CO-NH(CH_2)_4NH-CO$ |
| 416 | H | $PhCH_2$ | $PhCH_2$ | H | $PhCH_2$ | $PhCH_2$ | O | $CO-NH(CH_2)_6NH-CO$ |
| 417 | H | $PhCH_2$ | $PhCH_2$ | H | $PhCH_2$ | $PhCH_2$ | O | $CO-N(C_2H_4)N-CO$ |
| 418 | H | $PhCH_2$ | $PhCH_2$ | H | $PhCH_2$ | $PhCH_2$ | H | $CO-NH(CH_2)_2NH-CO$ |
| 419 | H | $PhCH_2$ | $PhCH_2$ | H | $PhCH_2$ | $PhCH_2$ | H | $CO-NH(CH_2)_4NH-CO$ |
| 420 | H | $PhCH_2$ | $PhCH_2$ | H | $PhCH_2$ | $PhCH_2$ | H | $CO-NH(CH_2)_6NH-CO$ |
| 421 | H | $PhCH_2$ | $PhCH_2$ | H | $PhCH_2$ | $PhCH_2$ | H | $CO-N(C_2H_4)N-CO$ |
| 422 | Ph | H | $PhCH_2$ | Ph | H | $PhCH_2$ | O | $CO-NH(CH_2)_2NH-CO$ |
| 423 | Ph | H | $PhCH_2$ | Ph | H | $PhCH_2$ | O | $CO-NH(CH_2)_4NH-CO$ |
| 424 | Ph | H | $PhCH_2$ | Ph | H | $PhCH_2$ | O | $CO-NH(CH_2)_6NH-CO$ |
| 425 | Ph | H | $PhCH_2$ | Ph | H | $PhCH_2$ | O | $CO-N(C_2H_4)N-CO$ |
| 426 | Ph | H | $PhCH_2$ | Ph | H | $PhCH_2$ | H | $CO-NH(CH_2)_2NH-CO$ |
| 427 | Ph | H | $PhCH_2$ | Ph | H | $PhCH_2$ | H | $CO-NH(CH_2)_4NH-CO$ |
| 428 | Ph | H | $PhCH_2$ | Ph | H | $PhCH_2$ | H | $CO-NH(CH_2)_6NH-CO$ |
| 429 | Ph | H | $PhCH_2$ | Ph | H | $PhCH_2$ | H | $CO-N(C_2H_4)N-CO$ |
| 430 | Ph | H | $PhCH_2$ | Ph | H | $PhCH_2$ | H | $CO-NH(CH_2)_2NH-CO$ |
| 431 | Ph | H | $PhCH_2$ | Ph | H | $PhCH_2$ | H | $CO-NH(CH_2)_4NH-CO$ |
| 432 | Ph | H | $PhCH_2$ | Ph | H | $PhCH_2$ | H | $CO-NH(CH_2)_6NH-CO$ |
| 433 | Ph | H | $PhCH_2$ | Ph | H | $PhCH_2$ | H | $CO-N(C_2H_4)N-CO$ |
| 434 | Ph | H | Ph | Ph | H | Ph | O | $CO-NH(CH_2)_2NH-CO$ |
| 435 | Ph | H | Ph | Ph | H | Ph | O | $CO-NH(CH_2)_4NH-CO$ |
| 436 | Ph | H | Ph | Ph | H | Ph | O | $CO-NH(CH_2)_6NH-CO$ |
| 437 | Ph | H | Ph | Ph | H | Ph | O | $CO-N(C_2H_4)N-CO$ |
| 438 | $NO_2-Ph$ | H | Ph | $NO_2-Ph$ | H | Ph | O | $CO-NH(CH_2)_2NH-CO$ |
| 439 | $NO_2-Ph$ | H | Ph | $NO_2-Ph$ | H | Ph | O | $CO-NH(CH_2)_3NH-CO$ |
| 440 | $NO_2-Ph$ | H | Ph | $NO_2-Ph$ | H | Ph | O | $CO-NH(CH_2)_4NH-CO$ |
| 441 | $NO_2-Ph$ | H | Ph | $NO_2-Ph$ | H | Ph | O | $CO-NH(CH_2)_5NH-CO$ |
| 442 | $NO_2-Ph$ | H | Ph | $NO_2-Ph$ | H | Ph | O | $CO-NH(CH_2)_6NH-CO$ |
| 443 | $NO_2-Ph$ | H | Ph | $NH_2-Ph$ | H | Ph | O | $CO-N(C_2H_4)N-CO$ |
| 444 | $NH_2-Ph$ | H | Ph | $NH_2-Ph$ | H | Ph | O | $CO-NH(CH_2)_2NH-CO$ |
| 445 | $NH_2-Ph$ | H | Ph | $NH_2-Ph$ | H | Ph | O | $CO-NH(CH_2)_3NH-CO$ |
| 446 | $NH_2-Ph$ | H | Ph | $NH_2-Ph$ | H | Ph | O | $CO-NH(CH_2)_4NH-CO$ |
| 447 | $NH_2-Ph$ | H | Ph | $NH_2-Ph$ | H | Ph | O | $CO-NH(CH_2)_5NH-CO$ |
| 448 | $NH_2-Ph$ | H | Ph | $NH_2-Ph$ | H | Ph | O | $CO-NH(CH_2)_6NH-CO$ |
| 449 | $NH_2-Ph$ | H | Ph | $NH_2-Ph$ | H | Ph | O | $CO-N(C_2H_4)N-CO$ |
| 450 | $NO_2-Ph$ | H | Ph | $NO_2-Ph$ | H | Ph | H | $CO-NH(CH_2)_2NH-CO$ |
| 451 | $NO_2-Ph$ | H | Ph | $NO_2-Ph$ | H | Ph | H | $CO-NH(CH_2)_3NH-CO$ |
| 452 | $NO_2-Ph$ | H | Ph | $NO_2-Ph$ | H | Ph | H | $CO-NH(CH_2)_4NH-CO$ |
| 453 | $NO_2-Ph$ | H | Ph | $NO_2-Ph$ | H | Ph | H | $CO-NH(CH_2)_5NH-CO$ |
| 454 | $NO_2-Ph$ | H | Ph | $NO_2-Ph$ | H | Ph | H | $CO-NH(CH_2)_6NH-CO$ |
| 455 | $NO_2-Ph$ | H | Ph | $NH_2-Ph$ | H | Ph | H | $CO-N(C_2H_4)N-CO$ |
| 456 | $NH_2-Ph$ | H | Ph | $NH_2-Ph$ | H | Ph | H | $CO-NH(CH_2)_2NH-CO$ |
| 457 | $NH_2-Ph$ | H | Ph | $NH_2-Ph$ | H | Ph | H | $CO-NH(CH_2)_3NH-CO$ |
| 458 | $NH_2-Ph$ | H | Ph | $NH_2-Ph$ | H | Ph | H | $CO-NH(CH_2)_4NH-CO$ |
| 459 | $NH_2-Ph$ | H | Ph | $NH_2-Ph$ | H | Ph | H | $CO-NH(CH_2)_5NH-CO$ |
| 460 | $NH_2-Ph$ | H | Ph | $NH_2-Ph$ | H | Ph | H | $CO-NH(CH_2)_6NH-CO$ |
| 461 | $NH_2-Ph$ | H | Ph | $NH_2-Ph$ | H | Ph | H | $CO-N(C_2H_4)N-CO$ |

In particular, as far as the dimers of formula (II) and (III) are concerned, all the possible combinations of the stereoisomers are possible, although not exactly specified in the above Table 3 and 4.

Furthermore, the present invention refers to the derivatives of 3-aza-bicyclo[3.2.1]octanes and their dimers that were prepared by the Applicants and described here for the first time, i.e. the 3-aza-bicyclo[3.2.1]octane derivatives (I) and their dimers of general formula (II) and (III) defined as above with exclusion of the following compounds: 1, 2, 5, 7, 8, 9, 10, 12, 13, 17, 19, 20, 21, 32, 34, 35, 36, 38, 40, 44, 58, 60, 64, 65, 66, 70, 75, 76, 77, 78, 79 83, 87, 91, 95, 99, 101, 103, 138, 145, 152, 154, 163, 164, 168, 172, 174, 176, 178, 184, 186, 192, 322, 324.

The compounds above cited are indeed already described in *J. Org. Chem.* 1999, 64, 7347, *Organic Letters*, 2000, 2, 3987-3990, *Bioorganic & Med Chem* 2001, 9, 1625-1632, *Eur. J. Org. Chem.* 2002, 873-880, and in the European Application Patent No. 00104135.9-2117 and in the International Application No. WO 01/64686; in such documents the preparation methods of the compounds are also described.

The novel derivatives of 3-aza-bicyclo[3.2.1]octanes of general formula (I) and their dimers of general formula (II) and (III) may be prepared with the following process. The new compounds of general formula (I) and their correspondent dimers of formula (II) and (III), described for the first time in the present application may be prepared according the procedure described as following and represented in the following Scheme 1:

the enantiomers S,S were prepared analogously) or amine 8 (in the scheme 1 are shown only the R,S enantiomers, but the S,R enantiomers were prepared analogously). In the case of amide alcohol 9 the correspondent aldehyde or ketone 10 are obtained by oxidation. When $R_3$ is H in the amine 8, a Fmoc protection can be made. The further cyclisation of compounds 7, 8 e 10 (Scheme 1) occurs by treatment with $SOCl_2$ and MeOH (reaction condition i) followed by treatment with sulfuric acid adsorbed on $SiO_2$ in refluxing toluene (reaction conditions ii) or by treatment with trifluoro acetic acid (TFA)

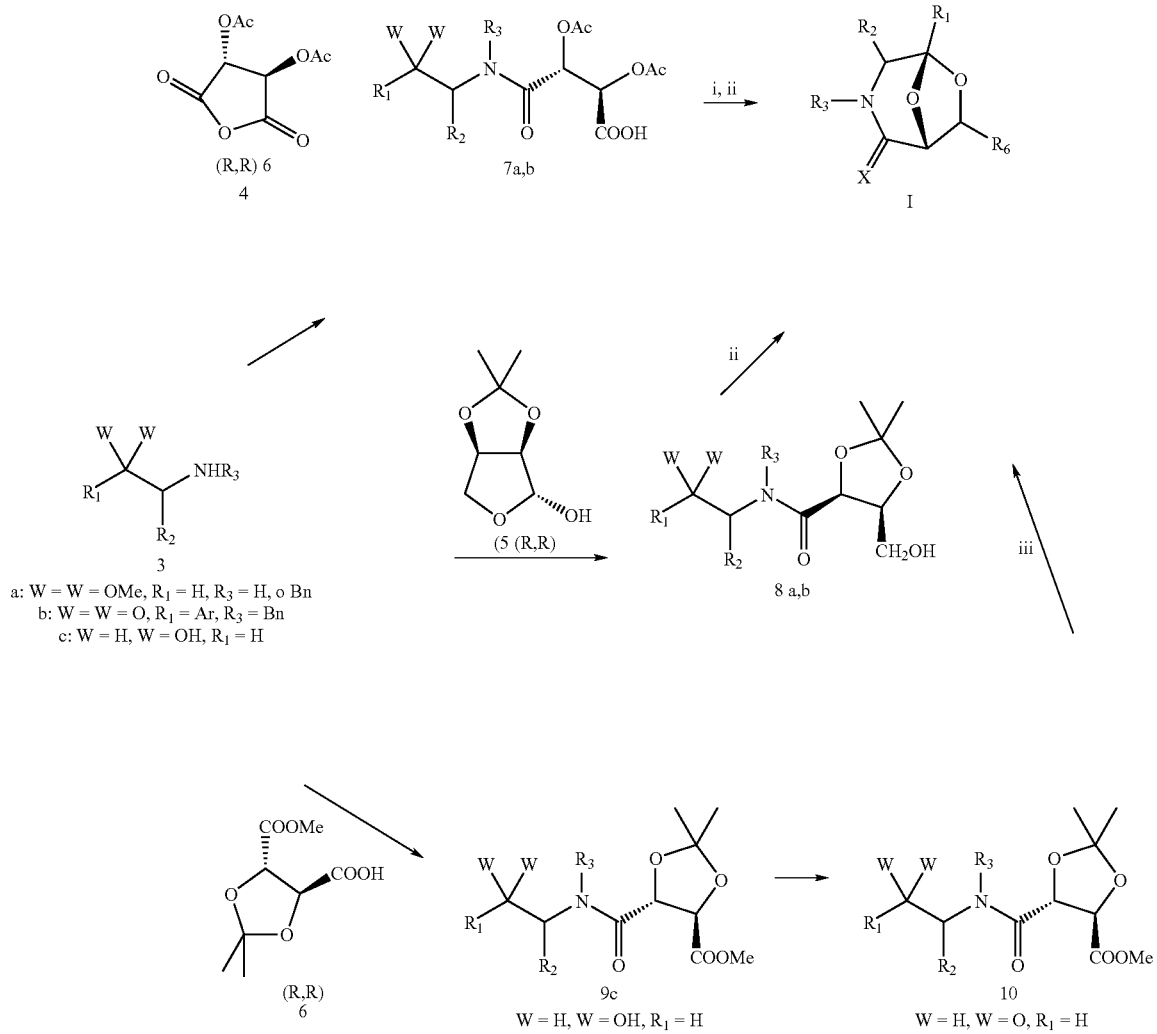

Protected alpha amino aldehydes (3a) or alpha amino ketones (3b) or alpha amino alcohols (3c) were reacted with—activated derivatives of tartaric acid as for example diacetyloxytartaric anydride 4 (R,R or S,S),—or with acid tartaric derivatives as for example the protected mono-methylester 6 (R,R or S,S), in the presence of coupling and activating agents—or by reductive amination with protected derivatives of erithrolactole 5 (R, R prepared from D-arabinose or S,S prepared from L-arabinose). The correspondent amides 7 e 9 (in the scheme 1 are shown only the R, R enantiomers, but pure or in methylene chloride (reaction conditions iii). Thus, starting from amides 7 and 10, the compounds I wherein X=O and $R_6$=—COOMe in configuration exo were prepared. In the case of amine 8 compounds I, wherein X=H, H and the group $R_6$=—$CH_2OH$ in endo configuration were prepared. The configuration R,R or S,S of stereocenters at C-1 bridgehead and at C-7 (bearing the carboxylic or hydroxymethyl group) is depending from that of tartaric acid or from starting erithrolactole. The compounds I may be modified according to Scheme 2.

SCHEME 2
The compounds of formula (I) (amide type), wherein X = O may be reduced, by

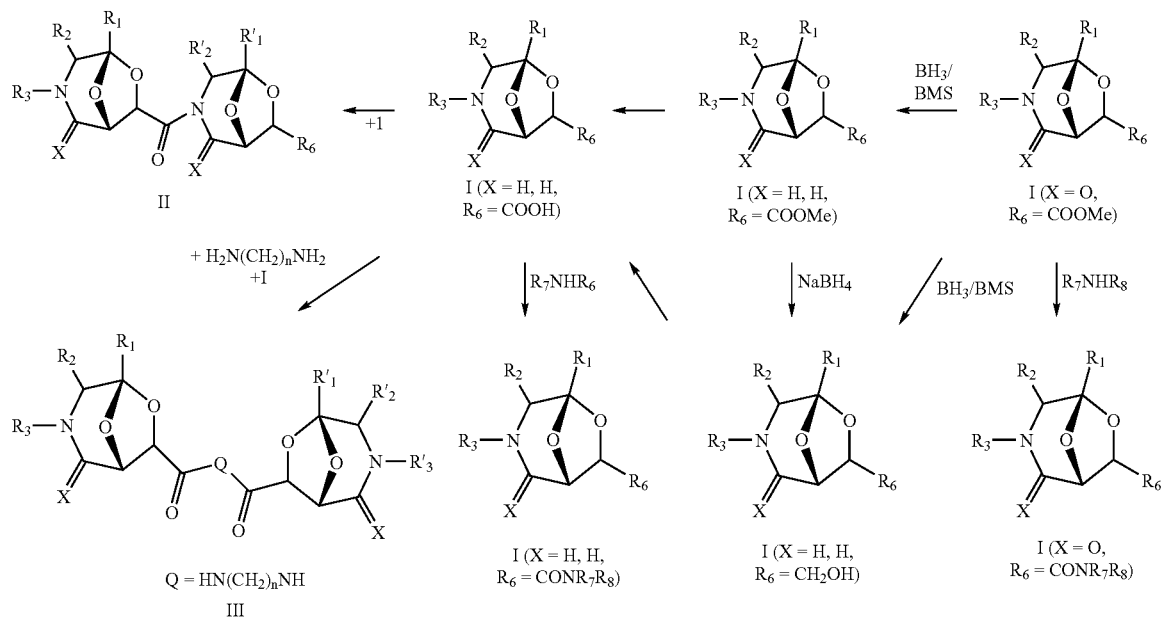

using the complex BH$_3$ dimethyl sulfide, either to correspondent amino esters I (X=H, H, R$_6$=COOMe), or to correspondent amino alcohol I (X=H, H e R$_6$=CH$_2$OH). Such compounds may be deprotected to nitrogen atom. The hydrolysis of amino ester I (X=H, H, R=COOMe) may be done either in acid or basic conditions, giving to the correspondent amino acid I (X=H, H e R$_6$=COOH). The amino acid is also obtained by Jones oxidation or by using PDC in DMF, from amino alcohol I (X=H, H e R$_6$=CH$_2$OH), also after the change of the benzyl group to Boc or Fmoc. By activation of the carboxylic group an amide bond with an amine NHR$_7$R$_8$ or an amino acid is formed. Otherwise, the activated carboxylic group of the amino acid I, is reacted with another unit of I having the deprotected nitrogen, to give the dimers of general formula (II) present in Table 3.

Otherwise, two units of a compound of formula (I) in each form, is reacted with a spacer Q, to give the dimers of general formula (III). The example shown in the scheme 2 includes but is not limited to the reaction of a diamine (Q) with two units of an activated carboxylic acid to give dimers of formula (III) reported in Table 4. The present 3-aza-bicyclo[3.2.1]octane derivatives of general formula (I) and their dimers of general formula (II) and (III), in free form or in form of pharmaceutically acceptable salts, may be used for preparation of pharmaceutical compositions following usual methods of pharmaceutical preparation.

Such pharmaceutical compositions may be formulated in conventional way, and may include one or more eccipients and/or diluent pharmaceutically acceptable. Administration of such formulations is feasible through any conventional route, such as parenteral, in the form of solution or suspension, oral, ocular, nasal, topical, etc.

The formulation of the 3-aza-bicyclo[3.2.1]octane derivatives of formula (I) and of their dimers of formula (II) and (III) according to the invention include tablets, capsules, pills, pellets, solutions, dispersions, suspensions, liposomal formulations, microspheres, nanospheres, creams and ointments, emulsions and aerosols, that can also be prepared in a way that allows a controlled or retarded release of the active compound.

Such pharmaceutical compositions may comprise at least one among the present compounds of formula (I), (II) and (III), or mixtures thereof, as active principle, possibly even in combination with other active principle or co-adjuvant, selected according to the pathologic conditions.

The pharmaceutical compositions comprising the compounds of the invention are suitable for pharmaceutical treatment of pathologic conditions related to the activity of neurotrophins.

The present derivatives of 3-aza-bicyclo[3.2.1]octane derivatives of general formula (I) and their dimers of general formula (II) showed neurotrophin agonist activity, especially of NGF, as they have the property of interacting with the NGF receptor complex at defined affinity levels. The agonist compounds have the property of inducing the biological signal of neurotrophins. The neurotrophin agonist compounds are suitable for, e.g., preparation of pharmaceutical compositions useful in the treatment of:

i) neurodegenerative, inflammatory, toxic, traumatic, or vascular disorders of the central, peripheral, or autonomic nervous system (such as Alzheimer Disease (AD), Amyotrophic Lateral Sclerosis (ALS), Huntington disease, multiple sclerosis, epilepsy, Down syndrome, nervous deafness, Ménière's disease), neural damages secondary to hypoxia, ischaemia, burns, chemotherapy, toxic compounds of various origin (including alcohol), infections (such as polio or HIV virus), trauma (including surgical trauma) originating axotomy of motoneurons, sensorial, motor, or sensorimotor neuropathies, or autonomic dysfunctions secondary to diverse pathologies (such as diabetes, renal insufficiency, or other systemic diseases), genetic disorders (such as Charcot- Marie-Tooth disease, Refsum disease, abetalipoprotenemia, Tangier disease, Krabbe disease, metachromatic leukodystrophy, Fabry disease, Dejerine-Softas disease), nervous pathologies of diverse origin (such as diffuse athrophy of cerebral cortex, Lewy body dementia, Pick's disease, mesolimbocortical dementia, neuronal ceroid lipofuscinosis, thalamic degeneration, cortico-striatal-spinal degeneration, cortico-basal ganglionic degeneration, cerebro-cerebellar degeneration, familial dementia with spastic paraparesis, pdlyglucosan bodies disease, Shy-Drager synfrome, olivopontocerebellar atrophy, progressive supranuclear palsy, deforming muscular dystony, Hallervorden-Spatz disease, Meige's syndrome, familial shivering, Gilles de la Tourette syndrome, chorea-acanthocytosis syndrome, Friedreich's ataxia, Holmes' corticocerebellar familial atrophy, Gerstmann-Straussler-Scheinker disease, progressive spinal muscular atrophy, spastic paraplegia, peroneal muscular atrophy, hypertrophic interstitial polyneuropathy, polyneuritic ataxic heredopathy), some ocular pathologies (such as optic nerve neuropathies, retinal degeneration, ophtalmoplegy, glaucoma), corneal diseases of diverse origin (such as neurotrophic, ulcers, post-traumatic or post-infective corneal disorders), pathologies from reduced motility of the gastrointestinal tract or from urinary bladder atony (such as interstitial cystitis or diabetic cystitis), endocrine neoplastic pathologies (such as prolactinoma), clinical conditions in which stimulation of learning processes is advantageous (in particular, in dementias and in post-traumatic conditions), besides all pathological conditions originating from apoptotic processes of neural cells;

ii) acquired immunodeficiency diseases due to reduced or absent bioavailability of NGF (such immunodificiency of ageing);

iii) conditions in which stimulation of neoangiogenesis may be advantageous (such as myocardial infarction, stroke, cerebral aneurysms, gastro-duodenal ulcers, wound healing, peripheral vasculopathies);

iv) certain ocular pathologies (such as corneal pathologies of diverse origin and glaucoma).

The present 3-aza-bicyclo[3.2.1]octane derivatives of general formula (I), and their dimers of general formula (II) and (III) above reported, are also suitable for the preparation of culture and storage media useful for conservation of explanted corneas destined to transplantation.

Moreover, when labelled with suitable reagents (contrast agents, radioisotopes, fluorescent agents, etc.), and possibly processed with any other procedure useful for medical imaging purposes, the present 3-aza-bicyclo[3.2.1]octane derivatives of general formula (I), and their dimers of general formula (II) and (III), may be used for the imaging analysis of tissues and organs containing neurotrophine receptors, either in vitro or in vivo. In particular such labelled compounds may be used either for monitoring the use and efficacy of drugs or for the diagnosis of mammal diseases in which the neurothrophine receptors are involved.

In general, the present compounds having neurotrophin agonistic activity, in particular NGF agonistic activity, were proven adequate to substitute for neurotrophin and NGF biologic activity.

Furthermore, the present neurotrophin agonistic compounds can be used to promote in vivo, in vitro, or ex vivo growth and/or survival of neural cells, including, but not limited to: dopaminergic, cholinergic, sensorial neurons, striatal cells, cortical cells, cells of the corpus striatum, hippocampus, cerebellum, olfactory bulbs, peri-aqueductal cells, cells of the raphe nuclei, of the locus coeruleus, of the dorsal root ganglia, sympathetic neurons, lower motoneurons, nervous stem cells, or cells anyhow deriving from the neural plaque.

The following examples are reported to give a non-limiting illustration of the present invention.

EXAMPLE 1

Preparation of methyl 3-benzyl-2-oxo-(1S,5S,7R)-6, 8-dioxa-3-azabicyclo[3.2.1]octane-7-exo-carboxylate (compound of formula (I) where X=O, $R_1$=H, $R_2$=Bn, $R_6$=(R)—COOMe) (Compound 1)

A solution of R,R tartaric anhydride 4 (4 g) (prepared as reported by Lucas H, J., Baumgarten W., *J. Am. Chem. Soc.*, 1941, 63, 1654) in anhydrous dichloromethane (23 ml) and 3a (where X=X=OMe, $R_1$=H, $R_2$=H, $R_3$=Bn,) (3 g) prepared as reported (Kermak, W. O.; Perkin, W. H.; Robinson, R. *J. Chem. Soc., Trans,* 1922, 121, 1872) were reacted at r.t. for 15 h. After evaporation of the solvent 7a (7 g), is obtained as an oil. To the crude product 7a in $CH_3OH$ (40 ml), thionyl chloride is added dropwise (0.8 ml) at 0° C. and then the mixture heated at 60° C. for 15 h. After evaporation of solvent, the crude product dissolved in toluene (8 ml) is quickly added to a refluxed suspension of (1.6 g) $H_2SO_4/SiO_2$ ($H_2SO_4$ 30% by weight) in toluene (12.5 ml). After 15 min, one third of the solvent is distilled off and the remaining hot mixture is filtered on a short pad of $NaHCO_3$. After evaporation of the solvent, the crude product was purified by chromatography giving the pure compound of the title (2.8 g).

$^1$H NMR ($CDCl_3$) δ 7.32-7.16 (m, 5H), 5.84 (d, J=2.0 Hz, 1H), 4.96 (s, 1H), 4.74 (s, 1H), 4.52 (s, 2H), 3.77 (s, 3H), 3.34 (dd, $J_1$=12.0 Hz, $J_2$=2.0 Hz, 2H), 3.08 (J=12.0 Hz, 1H). P.f. 82, $[\alpha]^{25}_D$=−49 (c 1.0, $CHCl_3$)

EXAMPLE 2

Preparation of methyl (1R,5R,7S)-3-benzyl-2-oxo-6, 8-dioxa-3-azabicylo[3.2.1]octane-7-exo-carboxylate (compound of formula (I) where X=O, $R_1$=$R_2$=H, $R_3$=Bn, $R_6$=(S)—COOMe) (Compound 191)

Following the same procedure of Example 1, starting from anhydride S,S tartaric 4, the compound of the title is obtained.

$^1$H NMR ($CDCl_3$) δ 7.40-7.10 (m, 5H), 5.85 (d, J=2.0 Hz, 1H), 4.97 (s, 1H), 4.74 (s, 1H), 4.52 (s, 2H), 3.79 (s, 3H), 3.34 (dd, $J_1$=12.0 Hz, $J_2$=2.0 Hz, 2H), 3.09 (J=12.0 Hz, 1H). P.f. 83, $[\alpha]^{25}_D$=+48 (c 1.0, $CHCl_3$)

EXAMPLE 3

Preparation of methyl (1S,5S,7R)-3-benzyl-6,8-dioxa-3-azabicyclo[3.2.1]octane-7-exo-carboxylate (compound of formula (I) where X=$R_1$=$R_2$=H, $R_3$=Bn, $R_6$=(R)—COOMe) (compound 40)

A solution of $BH_3.Me_2S$ (1 M, 2.5 ml,) was slowly added at 0° C. to a solution in anhydrous THF (65 ml) of compound of formula (I) where X=O, $R_1$=H, $R_2$=H, $R_3$=Bn, $R_6$=(R)—COOMe (compound 1) (2.8 g) prepared as described above in Example 1. The mixture was stirred for 18 h at r.t. and then ethanol (3 ml), NaOH solution (3M, 2 ml) and $H_2O$ (150 ml) were added. After extraction with diethylether, the organic phase was separated and evaporated giving, after chromatography, the pure compound of the title (2 g) as colorless oil.

¹H NMR (CDCl₃) δ 7.30-7.23 (m, 5H), 5.62 (s, 1H), 4.78 (s, 1H), 4.60, (s, 1H), 3.74 (s, 3H), 3.55 (pd, 2H), 2.84 (d, J=13 Hz, 1H), 2.76 (d, J=10 Hz, 1H), 2.50 (dd, J₁=10 Hz, J₂=2 Hz, 1H), 2.30 (d, J=11 Hz, 1H). [α]$^{25}_D$=−60 (c 1.0, CHCl₃).

EXAMPLE 4

Preparation of methyl (1S,5S,7R)-6,8-dioxa-3-azabicyclo[3.2.1]octane-7-exo-carboxylate (compound of formula (I) where X=R₁=R₂=R₃=H, R₆=(R)—COOMe) (Compound 34)

To a suspension of compound of formula (I) where X=R₁=R₂=H, R₃=Bn, R₆=(R)—COOMe) (compound 40) (2 g) prepared as described above in Example 3 and Pd/C 10% (1.3 g) in methanol (40 ml), is added ammonium formiate (2.4 g). The mixture left at reflux for 1 h, was filtered on Celite and washed with CH₃OH. The solution is evaporated to give the compound of the title (1.3 g), as colorless oil. ¹H NMR (CDCl₃), δ 5.53 (s, 1H), 4.72 (s, 1H), 4.49 (s, 1H), 3.71 (s, 3H), 3.17 (dd, J₁=13.6 Hz, J₂=1.8 Hz, 1H), 2.83 (m, 2H), 2.68 (d, J=13.6 Hz, 1H), 2.55 (br, 1H). [α]$^{25}_D$=−55 (c 0.7, CHCl₃).

EXAMPLE 5

Preparation of acid (1S,5S,7R)-6,8-dioxa-3-azabicylo[3.2.1]octane-7-exo-carboxylic (compound of formula (I) where X=R₁=R₂=R₃=H, R₆=(R)—COOH) (Compound 32)

The compound of formula (I) where X=R₁=R₂=R₃=H, R₆=(R)—COOMe (Compound 34) prepared as described in Example 4 (0.5 g) was dissolved in a solution of HCl (4N, 12 ml). After 18 h at r.t., the solution was evaporated obtaining the title compound as HCl salt (0.5 g).

[α]$^{25}_D$=−38.3 (c 1.1, H₂O); ¹H NMR (D₂O) δ 5.95 (s, 1H), 5.06 (s, 1H), 5.04 (s, 1H), 3.58 (m, 2H), 3.34 (m, 2H);

EXAMPLE 6

Preparation of methyl (1S,5S,7R)-3-ter-butoxycarbonyl-6,8-dioxa-3-azabicyclo[3.2.1]octane-7-exo-carboxylate (compound of formula (I) where X=R₁=R₂=H, R₃=Boc, R₆=(R)—COOMe) (Compound 42)

DIPEA (0.8 ml) and (BOC)₂O (1.1 g) were added to a solution in CH₂Cl₂ anhydrous (9 ml) and ethanol (3 ml) of the compound of formula (I) wherein X=R₁=R₂=R₃=H, R₆=(R)—COOMe (Compound 34) (0.8 g) prepared as described in Example 4. The reaction mixture was left for 18 h at r.t., the solvent was evaporated and the residue was treated with a solution of NaHSO₃ (5%) and extracted with diethylether. After evaporation of the solvent, the crude product was purified by chromatography to give the title compound (0.8 g) as white solid.

¹H NMR (CDCl₃) δ 5.64 and 5.58 (rotamers) (s, 1H), 4.65 and 4.60 (rotamers) (s, 1H), 4.51 (s, 1H), 3.72 (s, 3H), 4.00-3.60 (m, 2H), 3.20 (m, 1H), 2.92 (m, 1H), 1.43 (s, 9H).

EXAMPLE 7

Preparation of (1S,5S,7R)-3-ter-butoxycarbonyl-6,8-dioxa-7-exo-hydroxymethyl-3-azabicyclo[3.2.1]octane (compound of formula (I) where X=R₁=R₂=H, R₃=Boc, R₆=(R)—CH₂OH) (Compound 62)

To a solution in MeOH (15 ml) of the compound of formula (I) where X=R₁=R₂=H, R₃=Boc, R₆=(R)—COOMe) (Compound 42) (0.8 g) prepared as described in Example 6, at 0° C., NaBH₄ (0.6 g) was added in small portions. After 10 min at r.t., the mixture was evaporated, and the crude product was purified by chromatography to give the compound of the title (0.5 g) as a colourless oil. [α]$^{25}_D$−30 (c 1.0, MeOH).

¹H NMR (CDCl₃) δ 5.50 and 5.44 (rotamers) (s, 1H), 4.32 and 4.27 (rotamers) (s, 1H), 4.18 (m, 1H), 3.88-3.67 (m, 2H), 3.56 (d, J=5.5 Hz, 2H), 3.21 (m, 1H), 2.96 (m, H), 1.92 (b, 1H), 1.43 (s, 9H).

EXAMPLE 8

Preparation of (1S,5S,7R)-3-(9-Fluorenylmethoxycarbonyl)-7-endo-hydroxymethyl-6,8-dioxa-3-azabicyclo[3.2.1]octane (compound of formula (I) where X=R₁=R₂=H, R₃=Fmoc, R₆=(R)—CH₂OH) (Compound 61)

To a solution of 2,3-O-isopropylidene-D-erithrose (R,R) 5 (1.8 g) in THF (prepared from D-Arabinose, as reported by Thompson, D. K.; Hubert, C. N.; Wightman, R. H. *Tetrahedron* 1993, 49, 3827-3840) 2,2-diethoxyethylamine 3a (where W=W=OEt, R₁=R₂=R₃=H) (1.7 ml) a 0° C., NaBH (OAc)₃ (3.1 g) was added in small portions. After 18 h a r.t., the mixture is diluted with a saturated solution of NaHCO₃ and extracted with ethyl acetate. The organic phase was evaporated giving an oil, which was chromatographed to give the product 8a (where W=W=OEt, R₁=R₂=R₃=H) as yellowish oil (1.9 g).

[α]$^{20}_D$ −8.4 (c 0.54, CHCl₃); ¹H NMR (CDCl₃) δ 4.83 (br, 2H), 4.59 (t, J=5.5 Hz, 1H), 4.32 (m, 2H), 3.75-3.45 (m, 6H), 3.05-2.83 (m, 2H), 2.79 (d, J=5.5 Hz, 2H), 1.44 (s, 3H), 1.34 (s, 3H), 1.21 (t, J=7.0 Hz, 6H).

To a solution of 8a (where W=W=OEt, R₁=R₂=R₃=H) (1.7 g) in acetone (40 ml) Fmoc-O-Su (2.1 g) and an aqueous solution of Na₂CO₃.H₂O (0.75 g in 40 ml) were added at 0° C. The mixture was left at r.t. for 18 h, and extracted with CH₂Cl₂, then the solvent was evaporated and the residue was chromatographed to give the product 8a (where W=W=OEt, R₁=R₂=H, R₃=Fmoc) as yellowish oil (2.2-9). [α]$^{20}_D$ −34 (c 0.38, MeOH); ¹H NMR (CDCl₃) δ7.73 (d, J=7.3 Hz, 2H), 7.56 (m, 2H), 7.34 (m, 4H), 4.63 (m, 2H), 4.47-4.14 (m, 3H), 4.19 (t, J=4.9 Hz, 1H), 3.74-3.02 (m, 10H), 1.42-1.04 (m, 12H);

Compound 8a (where W=W=OEt, R₁=R₂=H, R₃=Fmoc) (1.9 g) dissolved in trifluoroacetic acid (8 ml) was left aside for 0.18 h a r.t. After evaporation of TFA, the crude compound, dissolved in MeOH, was filtered on as short pad of NaHCO₃, then the solvent was evaporated and the residue was chromatographed to, give the title product as a white solid (1 g).

M.p. 41-42° C.; [α]$^{20}_D$ −32 (c 0.5, CHCl₃); ¹H NMR (CDCl₃) δ7.77 (d, J=7.0 Hz, 2H), 7.57 (d, J=7.0 Hz, 2H), 7.38 (m, 4H), 5.51 (s, 1H), 4.92-2.95 (m, 12H).

EXAMPLE 9

Preparation of acid (1S,5S,7S)-3-(9-Fluorenyl-methoxycarbonyl)-6,8-dioxa-3-aza-bicyclo[3.2.1]octan-7-endo carboxylic (compound of formula (I) where $X=R_1=R_2=H$, $R_3=Fmoc$, $R_6=(S)-COOH$) (Compound 39)

To a solution of the compound of formula (I) where $X=R_1=R_2=H$, $R_3=Fmoc$, $R_6=(R)-CH_2OH$ (compound 61) (0.9 g) prepared according to the Example 8, in acetone (75 ml) was added the Jones reagent at 0° C., [prepared by slow addition of $H_2SO_4$ (2.8 ml) to a solution of $CrO_3$ (1.5 g) in $H_2O$ (20 ml) a 0°]. The mixture was left for 18 h at r.t and then was added with isopropanol, filtered on Celite and evaporated. The crude product dissolved in EtOAc (45 ml) was extracted with 10% $NaHCO_3$ in water. After separation, the aqueous phase was acidified at pH 1 with HCl and extracted with EtOAc. Evaporation of the organic phase gave a crude product which was chromatographed to give the compound of the title (0.7 g) as a white solid.

M.p. 79-82° C.; $[\alpha]^{20}_D$ −53 (c 0.5, $CHCl_3$); $^1H$ NMR ($CDCl_3$) δ 7.75 (m, 2H); 7.53 (d, J=7.0 Hz, 2H); 7.38 (m, 4H); 5.56 (s, 1H); 4.74-4.45 (m, 4H); 4.23-3.91 (m, 4H); 3.29-3.11 (m, 2H).

EXAMPLE 10

Preparation of (1R,5R,7R)-3-(9-Fluorenylmethoxycarbonyl)-6,8-dioxa-3-aza-bicyclo[3.2.1]octan-7-endo carboxylic acid (compound of formula (I) where $X=R_1=R_2=H$, $R_3=Fmoc$, $R_6=(R)-COOH$) (compound 218)

A solution of (1R,5R,7S)-3-(9-fluorenylmethoxycarbonyl)-7-endo-hydroxymethyl-6,8-dioxa-3-aza-bicyclo[3.2.1]octane (compound of formula (I) where $X=R_1=R_2=H$, $R_3=Fmoc$, $R_6=(S)-CH_2OH$) (1.8 g), prepared from (S,S) erythrose 5 (obtained starting from L-arabinose) with the same procedure above described in the Example 8 for its enantiomer, was treated as above described in the Example 9 for its enantiomer, to give 1.4 g of the title compound as white solid.

M.p. 71-81° C.; $[\alpha]^{20}_D$ +52.9 (c 0.50, $CHCl_3$).

EXAMPLE 11

Preparation of methyl 3-benzyl-5-phenyl-2-oxo-(1S,5S,7R-6,8-dioxa-3-azabicyclo[3.2.1]octane-7-exo-carboxylate (compound of formula (I) where $X=O$, $R_1=Ph$, $R_2=H$, $R_3=Bn$, $R_6=(R)-COOMe$) (Compound 27)

To a solution of 3b (2.4 g) (where $X=O$, $R_1=Ph$, $R_2=H$, $R_3=Bn$,) (prepared according the procedure reported by R Simonoff and W. H Hartung, J. Am. Pharm. Assoc., 35, 306, 1946) in dry $CH_2Cl_2$ (20 ml), (R,R) 6 acid tartaric derivative (2.49 g, 5.33 mmol) and DIPEA (5.4 ml) were added. The mixture was stirred at r.t. for 2 h, the solvent was evaporated to give an oil which was extracted in ethyl acetate. The solution was washed with solution of 5% $KHSO_4$, and 5% $NaHCO_3$ in water. After evaporation of the solvent the residue was purified by chromatography to give 8b (where $X=O$, $R_1=Ph$, $R_2=H$, $R_3=Bn$,) (3.2 g) as colourless oil.

$^1H$ NMR δ7.90-7.85 (m, 2H), 7.61-7.22 (m, 8H), 5.39 (d, J=5.1 Hz, 1H), 5.11 (d, J=5.1 Hz, 1H), 4.88-4.10 (m, 4H), 3.80 (s, 3H), 1.49 (s, 3H), 1.31 (s, 3H).

A solution of 8b (3.2 g) (where $X=O$, $R_1=Ph$, $R_2=H$, $R_3=Bn$,) in toluene (80 ml) was quickly added to a suspension of $H_2SO_4/SiO_2$ (30% w/w, 1.4 g) in toluene at reflux (120 ml). After 15 min one third of the solvent was distilled off and the hot remaining mixture was filtered on a short pad of $NaHCO_3$. After evaporation of the solvent the residue was purified by chromatography to give 2.4 g of the title compound as colorless solid.

M.p. 113-114° C. $[\alpha]^{25}_D$ −64.0 (c 1, $CDCl_3$). $^1H$ NMR δ 7.62-7.59 (m, 2H), 7.41-7.24 (m, 8H), 5.16 (s, 1H), 4.92 (s, 1H), 4.61 (m, 2H), 3.74 (s, 3H), 3.46 (m, 2H).

EXAMPLE 12

Preparation of methyl 3-benzyl-5-phenyl-(1S,5S,7R)-6,8-dioxa-3-azabicyclo[3.2.1]octane-7-exo-carboxylate (compound of formula (I) where $X=R_2=H$, $R_1=Ph$, $R_3=Bn$, $R_6=(R)-COOMe$) (Compound 120)

To a solution in dry THF (25 ml) of the compound of formula (I) where $X=O$, $R_1=Ph$, $R_2=H$, $R_3=Bn$, $R_6=(R)-COOMe$) (compound 27) prepared as described in Example 11 (2.5 mmol), at 0° C., $BH_3.Me_2S$ (10 M 0.5 ml, 4.9 mmol) was added dropwise. The mixture was left aside for 16 hr and then EtOH (1 ml), 3 M NaOH 1 ml) and $H_2O$ (20 ml) were added. After extraction with diethylether, and evaporation of the solvent the residue was purified by chromatography to give 1 g of the compound of the title as colorless solid.

M.p. 97° C. $[\alpha]_D^{25}$=13.0 (c 1, $CHCl_3$). $^1H$ NMR δ 7.72-7.58 (m, 2H), 7.52-7.19 (m, 8H), 5.00 (s, 1H), 4.86 (s, 1H), 3.75 (m 2H), 3.78 (s, 3H), 3.62 (m, 2H), 3.16 (d, J=11.2, 4H), 2.93 (d, J=11.6, 2H), 2.63 (d, J=11.0, 2H).

EXAMPLE 13

Preparation of methyl (1S,4S,7R)-3,4-Dibenzyl-2-oxo-6,8-dioxa-3-azabicyclo[3,2,1]octane-7-exo-carboxylate (compound of formula (I) where $X=O$, $R_1=H$, $R_2=(S)Bn$, $R_3=Bn$, $R_6=(R)-COOMe$) (Compound 12)

To a solution of L-phenylalaninol 3c (where W=H, W=OH, $R_1=H$, $R_2=Bn$, $R_3=H$) (5 g) in MeOH (150 ml) benzaldehyde (3.3 ml) were added. The reaction mixture was stirred at r.t. for 1 h, then 1.2 g of $NaBH_4$, were added in small portions in 2 hr at 0° C. The solvent was evaporated and the residue extracted with 50 ml of HCl at pH=2. The aqueous solution was extracted with $Et_2O$, treated with $Na_2CO_3$ until pH=9 and then extracted with $CHCl_3$. The organic phase evaporated gave N-benzyl-(L)-phenylalaninol as white solid (7 g) 3c (where W=H, W=OH, $R_1=H$, $R_2=Bn$, $R_3=Bn$)

$^1H$ NMR ($CDCl_3$) δ, ppm: 7.34-7.06 (m, 10H), 3.73 (s, 2H), 3.31 (dd, J=6.2, 12.5 Hz, 1H), 3.00-2.81 (m, 1H), 2.80-2.66 (m, 2H). 2.62 (dd, J=6.2, 12.5 Hz, 1H)

To a solution of N-benzyl-(L)-phenylalaninol 3c (2.8 g) in 23 ml of $CHCl_3$ at 0° C. DIPEA (4 ml), HOBt (2.1 ml) and a solution of methyl ester of (2R,3R)-2,3-O-isopropylidentartaric acid (6) (2.4 g) in 23 ml of $CHCl_3$, were added. Then 1.7 g of DIPC were added. After 72 hr at r.t, the solvent was evaporated and the crude product residue was purified by chromatography to give a yellowish solid (2.4 g) 9c (where W=H, W=OH, $R_1=H$, $R_2=Bn$, $R_3=Bn$).

$[\alpha]_D^{25}$ −72 (c=0.5, $CHCl_3$). $^1H$ NMR ($CDCl_3$), δ, ppm: (mixture of rotamers 2:1) major δ 7.40-7.05 (m, 10H), 5.28 (d, J=6.0 Hz, 1H), 4.81 (d, J=6.0 Hz, 1H), 4.75 (d, J=16.4 Hz, 1H), 4.0 (d, J=16.4 Hz, 1H), 3.79 (s, 3H), 3.70 (m, 1H), 3.60 (m, 1H), 3.46 (m, 1H), 3.04 (m, 1H), 1.52 (s, 3H), 1.49 (s, 3H).

The compound 9c (where W=H, W=OH, $R_1$=H, $R_2$=Bn, $R_3$=Bn) was oxidized to 10 (where W=O, W=O, $R_1$=H, $R_2$=Bn, $R_3$=Bn) by Swern oxidation. 4.5 g of alcohol (9c) in 20 ml of $CH_2Cl_2$ were oxidized as usual by treatment with oxalyl chloride, DMSO and DIPEA. After usual work-up compound (10) (5 g) was obtained as yellow solid.

$^1$H NMR (CDCl$_3$) δ ppm: 9.44 (s, 1H), 7.40-7.00 (m, 10H), 5.33 (d, J=6.2 Hz, 1H), 4.92 (d, J=6.2 Hz, 1H), 4.89 (d, J=18.7 Hz, 1H), 3.79 (s, 3H), 3.53 (dd, J=9.8, 4.3 Hz, 1H), 3.44 (d, J=18.7 Hz, 1H), 3.41 (dd, J=13.9, 4.3 Hz, 1H), 3.12 (dd, J=13.9, 9.8 Hz, 1H), 1.54 (s, 3H), 1.45 (s, 3H).

The product was added in toluene (15 ml), to a suspension of 2.5 g $SiO_2$ and $H_2SO_4$ in 30 ml of refluxing toluene; After 30 min, After 15 min one third of the solvent was distilled off and the hot remaining mixture was filtered on a short pad of $NaHCO_3$. After evaporation of the solvent the residue was purified by chromatography to give 3.2 g of the title compound.

$^1$H NMR (CDCl$_3$) δ ppm: 7.40-7.15 (m, 8H), 7.03 (m, 2H), 5.51 (s 1H), 5.33 (d, J=15.0 Hz, 1H), 4.97 (s, 1H), 4.71 (s, 1H), 4.03 (d, J=15.0 Hz, 1H), 3.75 (s, 3H), 3.32 (dd, J=10.7, 3.7 Hz, 3H), 3.15 (dd, J=13.5, 3.7 Hz, 1H), 2.75 (dd, J=13.5, 10.7 Hz, 1H)

EXAMPLE 14

Preparation of (1S,4S,7R)-3,4-Dibenzyl-6,8-dioxa-7-exo-hydroxymethyl 3-azabicyclo[3,2,1]octane (compound of formula (I) where X=$R_1$=H, $R_2$, (S)Bn, $R_3$=Bn, $R_6$=(R)—$CH_2OH$) (Compound 184)

To a solution in 100 ml of anhydrous THF of the compound of formula (I) where X=O, $R_1$=H, $R_2$=(S)Bn, $R_3$=Bn, $R_6$=(R)—COOMe (compound 12) (4 g), prepared as described in Example 13, a solution $BH_3.SMe_2$ (3 ml, 10 M) in THF was added. After 38 hr at r.t. the reaction mixture was treated with dry EtOH (6 ml) and 10% of NaOH (6 ml), then diluted with 50 ml of water and extracted with $Et_2O$. After evaporation of the solvent the residue was purified by chromatography to give 1.7 g of the title compound as yellowish solid. $[α]_D^{25}$ –59 (c=0.2, CHCl$_3$)

$^1$H NMR (CDCl$_3$) δ, ppm: 7.40-7.00 (m, 10H), 5.11 (s, 1H), 4.39 (t, J=5.1 Hz, 1H), 4.24 (s, 1H), 3.81 (d, J=13.6 Hz, 1H), 3.63 (d, J=13.6 Hz, 1H) 3.52 (m, 2H), 3.00 (m, 1H) 3.00-2.80 (m, 2H), 2.94 (d, J=11.6 Hz, 1H), 2.45 (dd, J=11.6, 1.8 Hz, 1H)

EXAMPLE 15

Preparation of Dimer of Formula (II) where $R_1$=$R_1'$=H, $R_2$=$R_3$=$R_2'$=Bn, $R_6$=(R)—COOMe (Compound 348)

0.1 ml of DIPEA were added to a solution in 0.3 ml of $CH_2Cl_2$ of the compound of formula (I) where X=$R_1$=H, $R_2$=(S)Bn, $R_3$=Bn, $R_6$=(R)—COOH (Compound 188) (0.1 g) obtained by hydrolysis of the corresponding methyl ester (Compound 172) according to the procedure in Example 5. Then, 0.2 g of PyBroP at 0° C. and 0.05 g (0.209 mmol) of the compound of formula (I) where X=$R_1$=$R_3$H, $R_2$=(S)—Bn, $R_6$=(R)—COOMe (Compound 178) were added. The mixture was stirred overnight, the solvent evaporated and the residue dissolved in 50 ml of AcOEt. After evaporation of the solvent the residue was purified by chromatography to give 0.07 g of the title compound as white solid.

EXAMPLE 16

Preparation of Dimer of Formula (III) where X=O, $R_1$=$R_1'$=p-$NO_2$Ph, $R_2$=$R_2'$=H, $R_3$=$R_3'$=Ph, Q'=(CONH)$CH_2$)$_6$CONH) (Compound 441)

20 mg of (1R,5S,7R)-5-(4-Nitro-phenyl)-3-phenyl-6,8-dioxa-3-aza-bicyclo[3.2.1]octane-7-carboxylic acid methyl ester of formula (I) (Compound 31) (0.054 mmol) were added to 125.5 mg (1.08 mmol, 20 eq) of 1,6-diamino-hexane and the mixture heated at 65° C. overnight. The crude is purified by chromatography ($CH_2Cl_2$-MeOH, 20:1+NEt$_3$ 1%), thus obtaining 8 mg (0.018 mmol, 34%) of a yellow solid corresponding to (1R,5S,7R)-5-(4-nitro-phenyl)-3-phenyl-6,8-dioxa-3-aza-bicyclo[3.2.1]octane-7-(6-amino-hexyl)amide, i.e. the compound of formula (I) where X=O, $R_1$ p-$NO_2$Ph, $R_2$=H, $R_3$=Ph, $R_6$=CONH($CH_2$)$_6$$NH_2$ (Compound 189) ($R_f$=0.32) and 4 mg (0.0051 mmol, 10%) of an orange solid corresponding to the dimeric compound of formula (III) of the title (Rf=0.67).

Compound 189: $^1$H NMR (CDCl$_3$, δ): 832 (d, 2H, J=8.4 Hz), 7.83 (d, 2H J=8.8 Hz), 7.30-7.22 (m, 2H), 6.90-6.79 (m, 3H), 6.25 (m, 1H), 5.05 (s, 1H), 4.74 (s, 1H), 3.81-3.70 (m, 2H), 3.28 (d, 1H, J=9.8 Hz,), 3.20-3.10 (m, 2H), 2.92 (d, 1H, J=11.6 Hz), 2.61 (m, 2H), 1.78-1.15 (m, 10H).

dimeric compound of formula (III) of the title: $^1$H NMR (CDCl$_3$, δ): 88 (d, 4H, J=8.8 Hz), 7.82 (d, 4H, J=10 Hz), 7.31-7.24 (m, 4H), 6.91-6.80 (m, 6H), 6.25 (m, 2H), 5.05 (s, 2H), 4.75 (s, 2H), 3.81-3.71 (m, 4H), 3.29 (d, 2H, J=11.6 Hz,), 3.20-3.10 (m, 4H), 2.92 (d, 2H, J=11.6 Hz), 1.54 (m, 4H), 1.23 (m, 4H).

Biological Activity

The biological activity of 3-aza-bicyclo(3.2.1)octanes of formula (I) and their dimeric forms of formula (II) and (III) was evaluated in different assays: induction of survival of PC12 cells in serum-free conditions, induction of proliferative activity in PC3 prostatic carcinoma cell line, induction of VGF polypeptide synthesis, displacement of 125I-NGF binding to specific surface receptor, and induction of Trk-A autophosphorylation. In all of these assays human recombinant (hr)NGF was used as internal standard.

Effect of Compounds on PC12 Cell Survival in Serum-Free Conditions.

The biological activity of 3-aza-bicyclo(3.2.1)octanes of formula (I) and their dimeric forms of formula (II) and (III) was tested as ability to induce the survival of PC12 cells in serum-free conditions by using hrNGF as internal standard. PC12 cells were detached from tissue flasks with PBS-EDTA (physiological saline solution added with ethylendiaminotetraacetic acid) and washed once with PBS to avoid residual amounts of serum. The cells were then diluted in RPMI-1640 medium without phenol red supplemented with penicillin and streptomycin and cultured in 96 well plates at the final concentration of 5×10$^3$/well. Standard curve was performed by adding in triplicate cultures different concentrations of hrNGF, in the range between 1-25 ng/ml. The compounds were instead added, in triplicate, at the final concentrations of 1, 10, 100 μM. The cells were then cultured for 60 hours at 37° C. in a humidified, 5% $CO_2$, atmosphere. Then 10 μl of (3-[4.5-dimethylthiazol-2yl]-2.5-diphenyltetrazolium bromide (MTT, 0.5 mg/ml in isopropanol) were added to each well and plates, protected from the light, were left at 37° C. for 4 hours. At the end of incubation, 100 μl of 50% dimethylformamide (in 20% SDS, pH 7.4) were added to each well. Colorimetric reaction was detected with a 96 well plate reader by recording the absorbance at 570 nm. Results were expressed as survival induced by compounds/spontaneous survival*100

FIG. 1 shows the results obtained with 10 μM of the most representative compounds and with 1 nM of hrNGF.

Effect of Compounds on Proliferative Activity of PC3 Cell Line.

The ability of 3-aza-bicyclo(3.2.1)octanes of formula (I) and their dimeric forms of formula (II) and (III) with substitutions reported in Table 1-4 to induce proliferation of PC3 cell line, in serum-free conditions, was tested by using hrNGF as internal standard.

Figure 2:
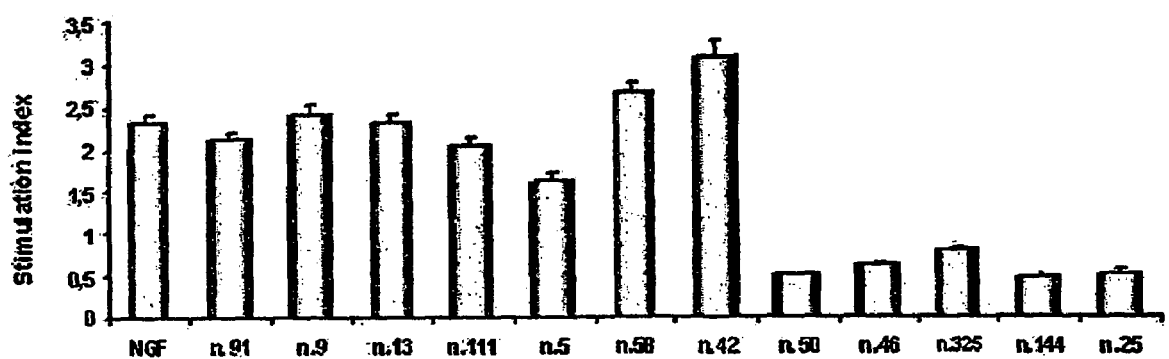
FIG. 2 shows the effect of present compounds on proliferative activity of PC3 cell line, in serum-free conditions, evaluated by using hrNGF as internal standard according to paragraph "Biological Activity". Results are expressed in terms of stimulation index, i.e. as ratio between $^3$H-thymidine incorporation (mean±SD) of stimulated cultures and $^3$H-thymidine incorporation of non stimulated cultures, for the compounds indicated on x axis.

PC3 cells were cultured in triplicate in 24 well plates at the final concentration of $10^4$ cells/ml (final volume of 500 μl) in RPMI 1640 medium in the presence or absence of 1, 10, 100 μM of the compounds or of different concentration (between 1-25 ng/ml) of hrNGF as internal standard. Cells were incubated for 60 hours in humidified, 5% $CO_2$, atmosphere. At the end of incubation 0.5 μCi of $^3$H-thymidine were added to each well for 8 hours. Cells were then washed 6 times with PBS, lysed with 0.1% Triton-X100 in 0.1 M phosphate buffer, and the radioactivity was recorded in a β-scintillation counter. Results were expressed as ratio between $^3$H-thymidine incorporation (mean±SD) of stimulated cultures and $^3$H-thymidine incorporation of non stimulated cultures. FIG. 2 shows the results obtained with 10 μM of selected compounds or with 1 nM hrNGF as internal standard.

Induction of VGF Production by PC12 Cells

The ability of 3-aza-bicyclo(3.2.1)octanes of formula (I) and their dimeric forms of formula (II) and (III) with substitution reported in Table 1-4 was tested also as ability to induce VGF production by PC12 cells. $5 \times 10^6$ PC12 cells were cultured in the presence or absence of 1, 10, 100 μM of the compounds or of 4 nM hrNGF as internal standard for 24 hours in humidified, 5% $CO_2$, atmosphere. Cells were lysed in 0.25% NP-40 in PBS supplemented with 1 mM PMSF (phenyl-methyl) and 1 mM leupeptin and protein concentration was measured in each sample by Bradford assay. Equal amounts of proteins (30 μg) were loaded in 8% SDS-polyacrilamide gel, electrophoresed, blotted onto nitrocellulose membrane and stained with monoclonal antibodies anti-VGF followed by peroxidase-conjugated anti-mouse IgG. Reaction was visualized by Enhanced Chemiluminiscent Reagent (ECL, Amersham) following the manufacturer instruction.

Figure 3:
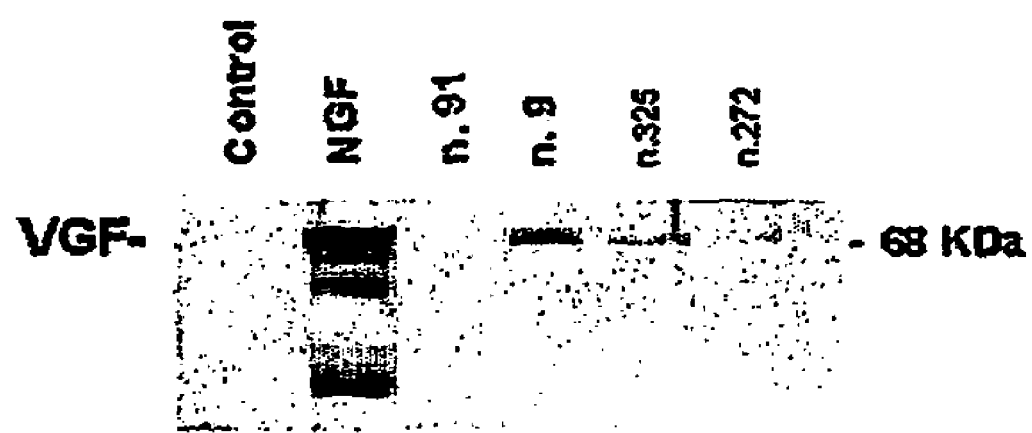
FIG. 3 illustrates the ability of present compounds (I), (II) and (III) to induce the VGF production by PC12 cells, evaluated as hereinafter described in paragraph "Biological Activity" in comparison with hrNGF. The control is 68 Kda VGF.

FIG. 3 shows the results obtained with 10 μM of the selected (n. 91, 9, 323, 270) compounds or with 10 nM hrNGF. VGF is induced by the selected compounds as well as by hrNGF.

Displacement of $^{125}$I-NGF Binding to PC12 Cells

The ability of selected compounds to displace the binding of NGF to specific surface receptor was evaluated through the classic binding techniques of iodinated ligand.

PC12 cells were detached from tissue flasks with PBS-EDTA, washed with HKR medium (10 mM Hepes, 125 mM NaCl, 4.8 mM KCl, 1.3 mM $CaCl_2$, 1.2 mM $MgSO_4$, 1.2 mM $KH_2PO_4$, 1 g/l glucose, 1 g/l BSA) and incubated in triplicate in HKR medium with 0.1 nM $^{125}$I-NGF in the presence or absence of variable concentrations of the compounds to be assayed or of hrNGF as internal standard. Displacement curve was obtained by analyzing the resultant cell bound radioactivity in the presence of the compounds or of hrNGF with adequate software (Graphit 4).

Figure 4A:
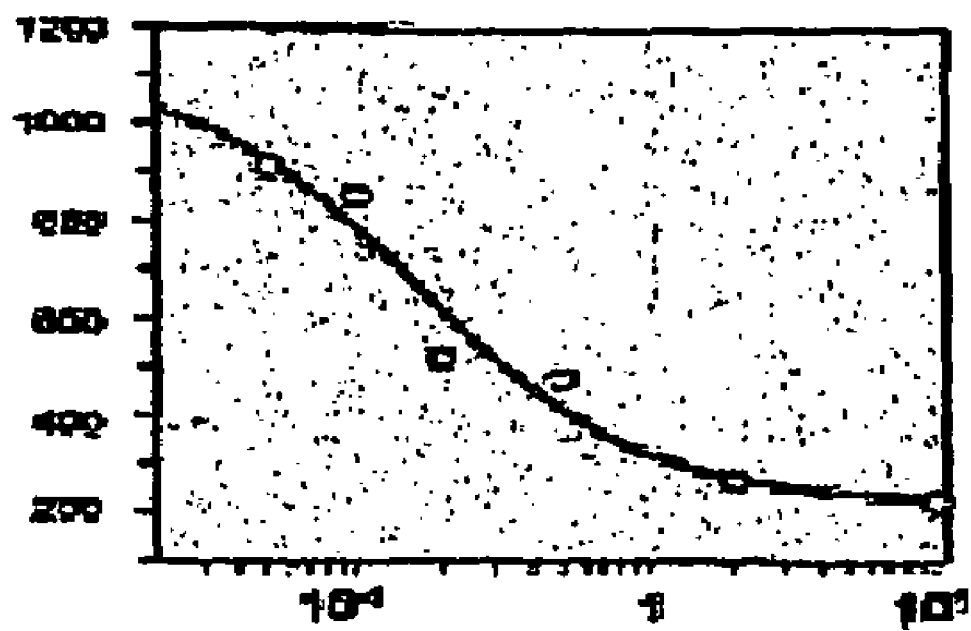
FIGS. 4a and 4b show the ability of present compounds to displace the $^{125}$I-NGF binding to PC12 cells, by a displacement curve obtained by analysing the resultant cell bound radioactivity in the presence of the present compounds or in the presence of hrNGF with adequate software (Graphit 4) according to paragraph "Biological Activity".
Figure 4B:
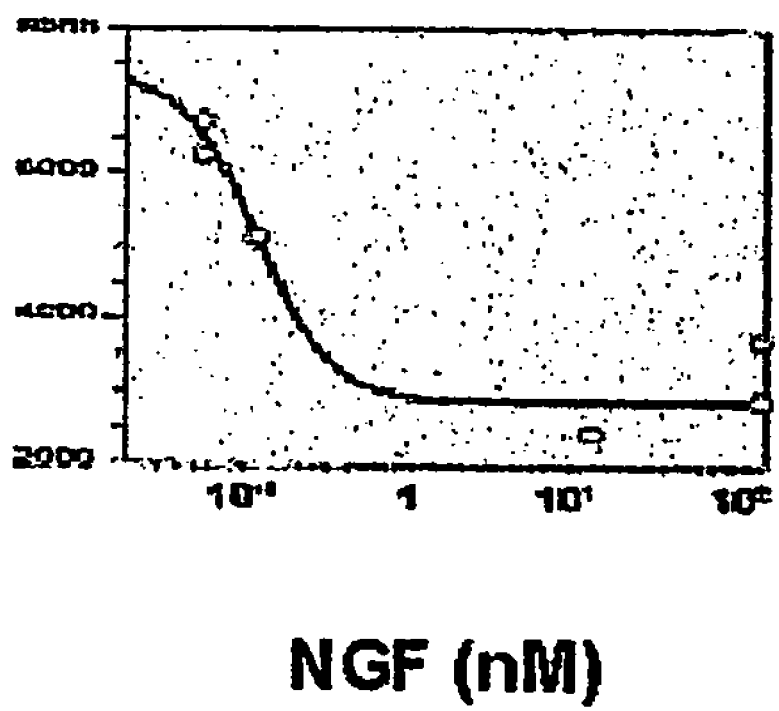

FIG. 4*a* shows the displacement curve obtained with the compound n.9 used as competitor The analysis of data revealed a Kd of 165 nM±0.05. FIG. 4*b* shows the displacement curve obtained by using hrNGF as competitor. The analysis of data revealed a Kd of 114 pM±0.01 as already reported.

Trk-A Autophosphorylation

To evaluate the ability of the compounds 3-aza-bicyclo (3.2.1)octanes of formula (I) and their dimeric forms of formula (II) and (III) reported in Table 14 to induce Trk-A autophosphorylation, PC12 cells were cultured in medium supplemented with 5% FBS for 48 hours, washed and equilibrated in serum-free medium for 2 hours. $2.5 \times 10^6$ cells were then stimulated with 10 μM of selected compounds for 30 min or with 10 nM hrNGF as positive control. Cells were then lysed with 0.5% Triton-X100 in PBS supplemented with protease inhibitors (PMSF, aprotinin, pepstatin, leupeptin) and phosphatase inhibitors. Protein concentrations in each sample was evaluated by Bradford assay and equal amounts (50 μg) of proteins were loaded onto SDS-polyacrilamide gel, electrophoresed and blotted onto nitrocellulose membrane. Membranes was stained with rabbit anti-(Tyr 490 and Tyr 674/675) phosphorylated Trk-A (Cell Signaling Technology) used at the final dilution of 1:1000. After washing, membranes were stained with HRP-conjugated anti-rabbit IgG and the reaction was visualised by using ECL reagents following manufacturing instructions.

Figure 5:
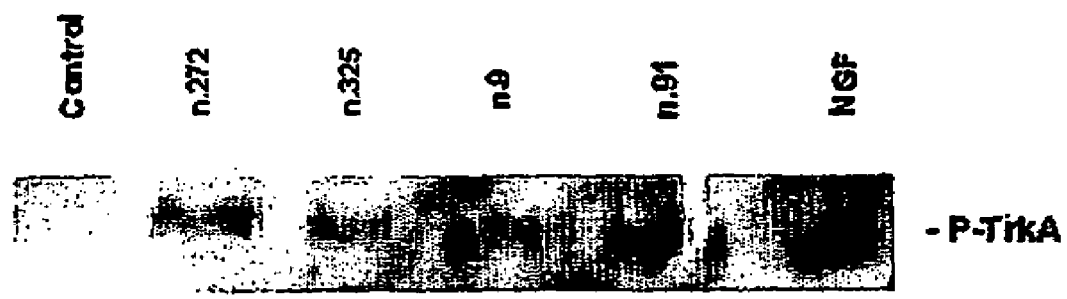
FIG. 5 shows the ability of the present compounds 272, 325, 9 and 91 to induce Trk-A autophosphorylation, by using hrNGF as internal standard according to paragraph "Biological Activity".

FIG. 5 shows the results obtained with the compounds 272, 325, 9, 91 and with hrNGF used as internal standard. The selected compounds are able to induce Trk-A autophosphorylation thus triggering the transduction of biological signals.

Synergic Activity

The synergic activity of multiple combinations of 3-aza-bicyclo(3.2.1)octanes of formula (I) and their dimeric forms of formula (II) and (III) was evaluated in the PC12 survival assay in serum-free condition.

Figure 6:
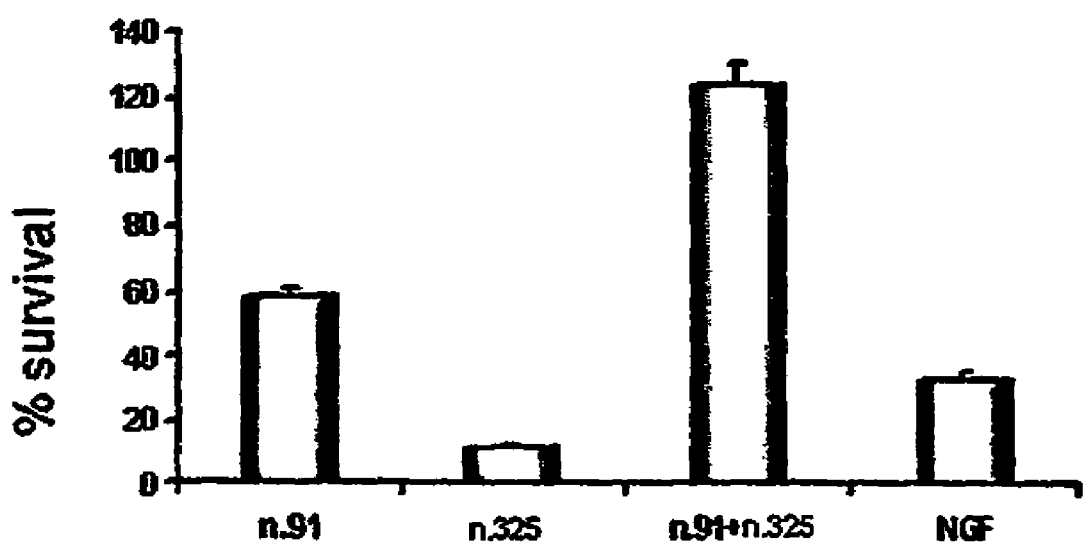
FIG. 6 shows the results obtained for the present compounds 9 and 325 and for the combination of the same two compounds, in a PC12 survival assay in serum-free condition, according to paragraph "Biological Activity". The results were expressed as survival induced by compounds/spontaneous survival*100.

PC12 cells were seeded in 96 well plates at the concentration of $5 \times 10^3$/well and cultured in triplicate in the presence or absence of 5 μM of selected compounds or of multiple combination of the same compounds at the final concentration of 10 μM. 0.5 nM hrNGF was used as internal standard. After 60 hours at 37° C. in a humidified, 5% $CO_2$, atmosphere, 10 μl of (3-[4.5-dimethylthiazol-2yl]-2.5-diphenyltetrazolium bromide (MTT, 0.5 mg/ml in isopropanol) were added to each well and plates, protected from the light, were left at 37° C. for 4 hours. At the end of incubation, 100 μl of 50% dimethyl-formammide (in 20% SDS, pH 7.4) were added to each well. Colorimetric reaction was detected with a 96 well plate reader by recording the absorbance at 570 nm. Results were expressed as survival induced by compounds/spontaneous survival*100. FIG. 6 shows as selected combinations of 2 compounds (91 and 325) induce survival activity higher than the addition of activities induced by the single compound.

The invention claimed is:

1. A pharmaceutical composition comprising as active principle at least one among the 3-aza-bicyclo[3.2.1]octane derivatives of general formula (I), or mixtures thereof

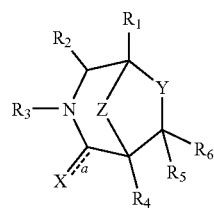

wherein:

$R_1$ is H, $R_2$ is selected from the group consisting of H, $C_{1-8}$alkyl, $C_{2-8}$alkenyl, $C_{2-8}$alkynyl, cycloalkyl, aryl, aryl$C_{1-8}$alkyl, heterocycle$C_{1-8}$alkyl, amino$C_{1-8}$alkyl, aminoaryl, $C_{1-8}$alkyloxyaryl, hydroxyaryl, hydroxy$C_{1-8}$ alkyl, carboxy$C_{1-8}$alkyl, methyloxycarbonyl$C_{1-8}$alkyl, carboxyaryl, carboalkyloxyaryl, alkylcarbamoylaryl and -(side chains of amino acids), or $R_3$ is selected from the group consisting of H, $C_{1-8}$alkyl, $C_{2-8}$alkenyl, $C_{2-8}$alkynyl, cycloalkyl, aryl, aryl$C_{1-8}$alkyl, heterocycle$C_{1-8}$alkyl, RR'N$C_{1-8}$alkyl, RR'Naryl, RO—$C_{1-8}$alkyl, RO(O)C—$C_{1-8}$alkyl, R(O)C—$C_{1-8}$alkyl, RC(O)O—$C_{1-8}$alkyl, RC(O)N(R)$C_{1-8}$alkyl, RO-aryl, RO(O)C-aryl, R(O)C-aryl RC(O)O-aryl, RC(O)N(R)aryl, —CH(amino acid side-chain)$CO_2$R, —CH(amino acid side-chain)C(O)NR, —CH($CO_2$R)— amino acid side-chain, CH(CONRR')— amino acid side-chain, Fmoc, Boc and Cbz, $R_4$, and $R_5$, equal or different amongst each other, are selected from the group consisting of H, $C_{1-8}$alkyl, $C_{2-8}$alkenyl, $C_{2-8}$alkinyl, cycloalkyl, aryl, heterocycle, aryl$C_{1-8}$alkyl and heterocycle$C_{1-8}$alkyl, $R_6$ is selected from the group consisting of H, $C_{1-8}$alkyl, $C_{2-8}$alkenyl, $C_{2-8}$alkynyl, cycloalkyl, aryl, aryl$C_{1-8}$alkyl, heterocycle, heterocycle$C_{1-8}$alkyl; —C(O)R, —C(O)OR, —C(O)NRR', $CH_2$OR, $CH_2$NRR', —C(O)NH—CH(amino acid side-chain)C(O)OR, $CH_2$NR-Fmoc, $CH_2$NR-Boc and $CH_2$NR—CBz, R and R', equal or different between each other, are selected from the group consisting of H, $C_{1-8}$alkyl, $C_{2-8}$alkenyl, $C_{2-8}$alkynyl, cycloalkyl, aryl, heterocycle, aryl$C_{1-8}$alkyl; heterocycle$C_{1-8}$alkyl; protecting group, —C(O)CH-(amino acid side-chain)-NHT, —NH—CH(amino acid side-chain)COOT and —CH(amino acid side-chain)COOT, where T is selected from between H and $C_{1-8}$alkyl;

X is O, α is a double bond,

Y and Z, equal or different from each other, are selected from the group consisting of O, S, SO, $SO_2$ and N—R, wherein R is as above defined;

Q is selected from the group consisting of C═O, $CH_2$, CO—NH—CH (amino acid side-chain)-CO, CONR$(CH_2)_n$CO, CONR—$C_{2-8}$alkenyl-CO C(O)O$(CH_2)$CO, $CH_2$OC(O)$(CH_2)$CO, and $CH_2$NRC(O)$(CH_2)_n$CO, wherein n is comprised between 2 and 6, and R is as above defined, Q' is selected from the group consisting of C(O)OCH_2, C(O)NRCH_2, $CH_2$OC(O), $CH_2$NRC(O), CONR$(CH_2)_n$NRCO, CONR—$C_{2-8}$alkenyl-NRCO, C(O)O$(CH_2)_n$NRCO, CONR$(CH_2)_n$OC(O), $CH_2$OC(O)$(CH_2)_n$OC(O)$CH_2$, $CH_2$NRC(O)$(CH_2)_n$NRC(O)$CH_2$, $CH_2$OC(O)$(CH_2)_n$NRC(O)$CH_2$, $CH_2$NRC(O)$(CH_2)_n$OC(O)$CH_2$, $CH_2$NR$(CH_2)_n$NRCH_2, $CH_2$O$(CH_2)_n$OCH_2, $CH_2$O$(CH_2)_n$NRCH_2, and $CH_2$NR$(CH_2)_n$OCH_2, wherein n is comprised between 2 and 6, and R is as above defined, and where the groups alkyl, alkenyl, alkynyl, cycloalkyl, aryl and the heterocyclic groups above reported, are possibly substituted; and a pharmaceutically acceptable excipient or diluent.

2. The pharmaceutical composition according to claim 1, wherein Z is O.

3. The pharmaceutical composition according to claim 1, wherein the alkyl, alkenyl, alkynyl, cycloalkyl, aryl and heterocyclic groups may be substituted with one or more moieties chosen from the group consisting of halogen, cyano, nitro, amino, hydroxy, carboxylic acid, carbonyl and $C_{1-6}$alkyl.

4. The pharmaceutical composition according to claim 1, wherein the 3-aza-bicyclo[3.2.1]octane derivatives of formula (I) are selected from the compounds having the following formulas:

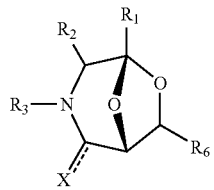

| Compound | X | $R_1$ | $R_2$ | $R_3$ | $R_6$ |
|---|---|---|---|---|---|
| 1 | O | H | H | $PhCH_2$ | (R) —$CO_2$Me |
| 2 | O | H | H | $PhCH_2$ | (S) —$CO_2$Me |
| 3 | O | H | H | $PhCH_2$ | (R)-CON⟨piperidine⟩ |
| 4 | O | H | H | $PhCH_2$ | (R) —CON⟨pyrrolidine⟩ |

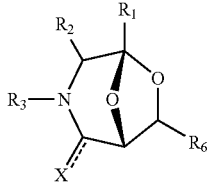

(I)

| Compound | X | R₁ | R₂ | R₃ | R₆ |
|---|---|---|---|---|---|
| 5 | O | H | (S) —Me | PhCH₂ | (R) —CO₂Me |
| 6 | O | H | (S) —Me | PhCH₂ | (S) —CO₂Me |
| 7 | O | H | (R) —Me | PhCH₂ | (R) —CO₂Me |
| 8 | O | H | (R) —Me | PhCH₂ | (S) —CO₂Me |
| 9 | O | H | (R) —CH₂Ph | PhCH₂ | (S) —CO₂Me |
| 10 | O | H | (R) —CH₂Ph | PhCH₂ | (R) —CO₂Me |
| 11 | O | H | (S) —CH₂Ph | PhCH₂ | (S) —CO₂Me |
| 12 | O | H | (S) —CH₂Ph | PhCH₂ | (R) —CO₂Me |
| 13 | O | H | (S) —CH₂OBn | PhCH₂ | (R) —CO₂Me |
| 14 | O | H | (S) —CH₂OBn | PhCH₂ | (S) —CO₂Me |
| 15 | O | H | (R) —CH₂OBn | PhCH₂ | (R) —CO₂Me |
| 16 | O | H | (R) —CH₂OBn | PhCH₂ | (S) —CO₂Me |
| 17 | O | H | (S) —CH₂OH | PhCH₂ | (R) —CO₂Me |
| 18 | O | H | (S) —CH₂OH | PhCH₂ | (S) —CO₂Me |
| 19 | O | H | (R) —CH₂OH | PhCH₂ | (R) —CO₂Me |
| 20 | O | H | (R) —CH₂OH | PhCH₂ | (S) —CO₂Me |
| 21 | O | H | =CH₂ | PhCH₂ | (R) —CO₂Me |
| 22 | O | H | =CH₂ | PhCH₂ | (S) —CO₂Me |
| 23 | O | H | (R) —CH₂OH | PhCH₂ | (S) —CO₂Me |

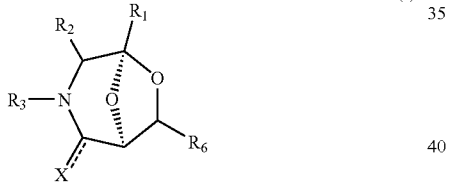

(I)

| Compound | X | R₁ | R₂ | R₃ | R₆ |
|---|---|---|---|---|---|
| 190 | O | H | H | PhCH₂ | (R) —CO₂Me |
| 191 | O | H | H | PhCH₂ | (S) —CO₂Me |
| 192 | O | H | (S) —Me | PhCH₂ | (R) —CO₂Me |
| 193 | O | H | (S) —Me | PhCH₂ | (S) —CO₂Me |
| 194 | O | H | (R) —Me | PhCH₂ | (R) —CO₂Me |
| 195 | O | H | (R) —Me | PhCH₂ | (S) —CO₂Me |
| 196 | O | H | (S) —PhCH₂ | PhCH₂ | (R) —CO₂Me |
| 197 | O | H | (S) —PhCH₂ | PhCH₂ | (S) —CO₂Me |
| 198 | O | H | (R) —PhCH₂ | PhCH₂ | (R) —CO₂Me |
| 199 | O | H | (R) —PhCH₂ | PhCH₂ | (S) —CO₂Me |
| 200 | O | H | (S) —CH₂CH(Me)₂ | PhCH₂ | (R) —CO₂Me |
| 201 | O | H | (S) —CH₂CH(Me)₂ | PhCH₂ | (S) —CO₂Me |
| 202 | O | H | (R) —CH₂CH(Me)₂ | PhCH₂ | (R) —CO₂Me |
| 203 | O | H | (R) —CH₂CH(Me)₂ | PhCH₂ | (S) —CO₂Me |
| 204 | O | H | H | PhCH₂ | (R) —CONHMe |
| 205 | O | H | H | PhCH₂ | (S) —CONHMe |
| 206 | O | H | (S) —Me | PhCH₂ | (R) —CONHMe |
| 207 | O | H | (S) —Me | PhCH₂ | (S) —CONHMe |

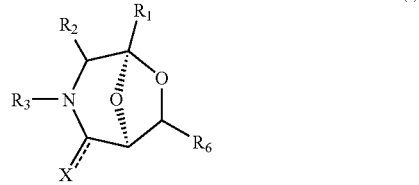

(I)

| Compound | X | R₁ | R₂ | R₃ | R₆ |
|---|---|---|---|---|---|
| 208 | O | H | (R) —Me | PhCH₂ | (R) —CONHMe |
| 209 | O | H | (R) —Me | PhCH₂ | (S) —CONHMe |
| 210 | O | H | (S) —PhCH₂ | PhCH₂ | (R) —CONHMe |
| 211 | O | H | (S) —PhCH₂ | PhCH₂ | (S) —CONHMe |
| 212 | O | H | (R) —PhCH₂ | PhCH₂ | (R) —CONHMe |
| 213 | O | H | (R) —PhCH₂ | PhCH₂ | (S) —CONHMe |
| 214 | O | H | (S) —CH₂CH(Me)₂ | PhCH₂ | (R) —CONHMe |
| 215 | O | H | (S) —CH₂CH(Me)₂ | PhCH₂ | (S) —CONHMe |
| 216 | O | H | (R) —CH₂CH(Me)₂ | PhCH₂ | (R) —CONHMe |
| 217 | O | H | (R) —CH₂CH(Me)₂ | PhCH₂ | (S) —CONHMe. |

5. The 3-aza-bicyclo[3.2.1]octane derivatives of formula (I) selected from the compounds indicated by the following numbers:
3, 4, 22-23, and 200-217, as defined in claim 4.

* * * * *